(12) United States Patent
Puskas et al.

(10) Patent No.: US 8,552,143 B2
(45) Date of Patent: Oct. 8, 2013

(54) METHOD FOR THE PREPARATION OF POLY (DISULFIDE) POLYMERS AND GELS

(75) Inventors: Judit E. Puskas, Akron, OH (US); Emily Q. Rosenthal, Akron, OH (US)

(73) Assignee: The University of Akron, Akron, OH (US)

(*) Notice: Subject to any disclaimer, the term of this patent is extended or adjusted under 35 U.S.C. 154(b) by 125 days.

(21) Appl. No.: 13/041,304

(22) Filed: Mar. 4, 2011

(65) Prior Publication Data

US 2011/0218298 A1  Sep. 8, 2011

Related U.S. Application Data

(60) Provisional application No. 61/310,354, filed on Mar. 4, 2010.

(51) Int. Cl.
| | | |
|---|---|---|
| C08F 6/06 | (2006.01) | |
| C08F 8/06 | (2006.01) | |
| C08J 3/03 | (2006.01) | |
| C08J 3/05 | (2006.01) | |
| C08G 75/14 | (2006.01) | |

(52) U.S. Cl.
USPC ........... 528/374; 528/373; 528/376; 528/492; 528/499

(58) Field of Classification Search
USPC .......................... 528/373, 374, 376, 492, 499
See application file for complete search history.

(56) References Cited

U.S. PATENT DOCUMENTS

| | | |
|---|---|---|
| 1,890,191 A | 12/1932 | Patrick |
| 1,996,486 A | 4/1935 | Patrick |
| 2,363,614 A | 4/1939 | Patrick |
| 2,553,206 A | 5/1951 | Patrick |
| 5,206,439 A | 4/1993 | Shaw |
| 5,464,931 A | 11/1995 | Shaw |
| 6,051,740 A | 4/2000 | Matson |

OTHER PUBLICATIONS

Garcia Ruano, José Luis, et al., Efficient synthesis of disulfides by air oxidation of thiols under sonication Green Chemistry, vol. 10 (May 9, 2008), pp. 706-711.
Heebeom Koo, et al., A new biodegradable crosslinked polyethylene oxide sulfide (PEOS) hydrogel for controlled drug release International Journal of Pharmaceutics, vol. 374, (Mar. 19, 2009), pp. 58-65.
Marvel, C.S., et al., Polyalkylene Disulfides (Downloaded by the University of Akron) vol. 79, (May 1, 2002), pp. 3089-3091.

(Continued)

*Primary Examiner* — Duc Truong
(74) *Attorney, Agent, or Firm* — Renner, Kenner, Greive, Bobak, Taylor & Weber

(57) ABSTRACT

High molecular weight disulfide polymers are synthesized in aqueous media by exposing dithiol compounds to a mild oxidizing environment in the presence of a tertiary amine catalyst. The unique oxidizing system polymerizes monomers through the formation of sulfur-sulfur bonds between dithiol compounds. The same oxidizing system may be used to make disulfide-crosslinked gels from compounds containing multiple thiol groups. The oxidizing system is comprised of oxygen at atmospheric concentration and dilute hydrogen peroxide. A filler such as carbon black may be incorporated into the polymer or cross-linked gel during polymerization. A polydisulfide polymer is provided having a weight average molecular weight of greater than about 100,000 g/mol and a polydispersity index of about 2 or less. A tetrathiol composition results from a reaction of a diacrylate with a trithiol. The tetrathiol composition may be subjected to an oxidizing environment with a tertiary amine catalyst to provide a polytetrathiol polymer network.

18 Claims, 33 Drawing Sheets

(56) References Cited

OTHER PUBLICATIONS

Kishore, K., et al., Polymers Containing Disulfide, Tetrasulfide, Diselenide and Ditelluride Linkages in the Main Chain Department of Inorganic and Physical Chemistry, Indian Institute of Science, India, Bangalore 560012, (Jun. 1, 1993), pp. 83-121.

Hanhela, P.J., et al., Thermal Stability of Sealants for Military Aircraft:—Modification of Polysulfide Prepolymners with Ether and Thzioether Monomers DSTO Materials Research Laboratory, Commonwealth of Australia 1993, AR No. 006-864, (Feb. 1993), pp. 7-26.

Koo, Heebeom, Synthesis of Poly(ethylene oxide sulfide) with Large Molecular Weight by O2 Gas Oxidation Bull. Korean Chem. Soc. 2005, vol. 26, No. 12 (Oct. 8, 2005), pp. 2069-2071.

Brian J. Evans, F NMR Study of the Reaction of p-Fluorobenzenethiol and Disulfide with Periodate and Other Selected Oxidizing Agents, J. Org. Chem. 1990, 55, 2337-2344.

METHOD FOR THE PREPARATION OF POLY(DISULFIDE) POLYMERS AND GELS

CROSS REFERENCE TO RELATED APPLICATIONS

This application claims benefit of U.S. Provisional Application No. 61/310,354 filed on Mar. 4, 2010.

STATEMENT REGARDING FEDERALLY SPONSORED RESEARCH OR DEVELOPMENT

This invention was made with government support under cooperative agreements awarded by National Science Foundation Grant number DMR 0509687. The government may have certain rights to the invention.

BACKGROUND OF THE INVENTION

The claimed invention relates to a novel, halide-free, environmentally-friendly (i.e., "green") method of producing organic poly(disulfide) polymers and networks through thiol oxidation. Polysufidic polymers are known in the art and are frequently referred to as "thiokols." Poly(disulfides) typically display high resistance to hydrocarbon solvents and have a low glass transition temperature. One previous method of polysulfide polymer synthesis focuses on the reaction of α,ω-dihalogenated compounds with polysulfide salts. The typical "Thiokol method" of polysulfide synthesis may be shown as follows:

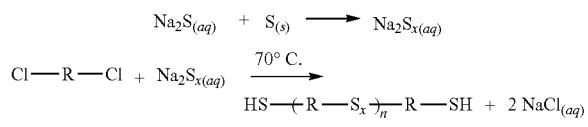

Disulfide and polysulfide bonds of the sulfide salt are created in situ prior to the reaction with the dihalide. The rank of sulfide bonds, from 1 to 5, is controlled by the method of synthesis. Many side reactions are possible in this method of synthesis. Some of the side reactions may be controlled to produce the desired end groups, or to tailor the molecular weight. The products of other side reactions, however, must be removed once the polymer has been formed.

Subsequent research has lead to other methods of preparation. Dithiols have been polymerized to polydisulfide polymers by oxygen alone, but the uncatalyzed reaction was too slow to become a practical industrial process, and high molecular weights were not achieved.

Oxygen- or air-induced oxidation of dithiols was previously known. One type of reaction included the addition of magnesium chloride and sodium hydroxide and often heated the reaction medium to boiling temperatures. Air oxidation has also been used to increase the molecular weight of previously synthesized polymers having terminal thiol groups. Neither molecular weight nor viscosity data were provided in published data. The texture of the resulting polymers was documented. For example, polymers created from the reaction of ethylene dichloride with sodium-sulfur salts were described as brittle, hard plastics, while the polymer formed from linear alkoxy halides were described as liquids or rubbers. Suspended dithiols (1-β-mercaptoethyl-3(or 4)-mercaptocyclohexane, 1-(α-methyl-β-mercaptoethyl-3-mercapto-4-methylcyclohexane, 1,6-hexanedithiol, 1,7-heptanedithiol, 1,9-nonanedithiol and 1,10-decanedithiol) in aqueous solutions of lauric acid and potassium hydroxide have been synthesized by bubbling compressed air through the emulsion for four to ten days. Selenious acid was also added as a catalyst in some polymerization reactions. Several other oxidizing agents (bromine, nitric acid, and ferric chloride) were investigated, but it was previously found that air oxidation produced polymers with the highest viscosities. The inherent viscosity (in chloroform) of the polymers as well as what they called the "softening temperature", which ranged from 45 to 130° C., were analyzed. The softening temperature may be comparable to what is currently known to as the glass transition in amorphous polymers and melting temperature in semicrystalline polymers.

Using a pure oxygen atmosphere, α,ω-thiol functionalized triethylene glycol and polyethylene glycol oligomers have been oxidized to linear polymers. The monomers and oligomers may be dissolved in an ammonia/methanol solvent mixture and exposed to pure oxygen gas atmosphere while stirring. After a 50 hour reaction period, the polymer from triethylene glycol reached $M_n$=61,000 g/mol. The polymer formed from the polyethylene glycol oligomer did not exceed ~40,000 g/mol.

Hydrogen peroxide may be used as an oxidizing agent in many synthetic organic chemistry reactions, including the oxidative polymerization of aniline and phenols and in the oxidation of small molecule thiols to disulfides. In the oxidation of thiols, the reaction does not stop at the disulfide, and may easily be over oxidized to form a sulfonic acid.

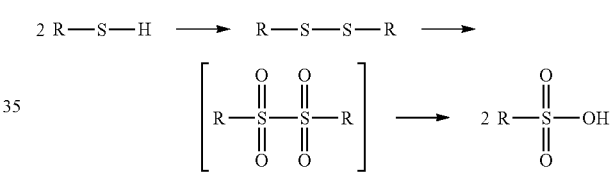

For this reason, it has been seen to have limited use as a thiol oxidizing agent. Reaction with hydrogen peroxide can also be a very exothermic reaction, which may make it unattractive for some purposes.

Hydrogen peroxide has been used as the oxidizing agent in the preparation of disulfide oligomers intended to modify Thiokol prepolymers. 2,2'-thiodiethanethiol or 2,2'-oxydiethanethiol was reacted with aqueous hydrogen peroxide in the presence of sodium hydroxide to produce colorless, viscous liquid oligomers of the corresponding dithiol. Molecular weight analysis of the oligomers was not provided in the published disclosure.

Hydrogen peroxide was also documented in dithiol polymerization reactions in other published techniques. However, the dithiol compounds were first reacted with elemental sulfur in the presence of a base. Also, the polymerization reaction was performed in an alcohol solution that contained an inorganic base like sodium hydroxide.

Triethylamine has been used as a catalyst for the air oxidation of thiols to disulfides dissolved in dimethyl formamide, and as a catalyst in the fragmentation polymerization reaction that combines dithiols and diacylsulfides to produce poly(disulfides).

While oxygen, hydrogen peroxide and triethylamine have been indicated in separate oxidative and oxidative polymerization reactions of dithiols to poly(disulfides), previous art documenting the combination of the three, without other additives, and leading to high molecular weight polymers has not been known. Additionally, other methods either use a chlorine-containing compound or an organic solvent as the reaction medium.

There is a need, therefore, for an alternate method for, synthesis of organic poly(disulfide) polymers. There is also a need for a method of synthesis of organic poly(disulfide) polymers that does not rely upon the use of a heavy metal catalyst or halogenated compounds. There is likewise a need for a method of synthesis of organic poly(disulfide) polymers that does not rely upon the use of an organic reaction media.

BRIEF SUMMARY OF THE INVENTION

It is, therefore, an aspect of the claimed invention to provide a method of synthesis of organic poly(disulfide) polymers that avoids dangerous or toxic oxidation methods by taking a synergistic approach to oxidation that combines the oxidizing capabilities of hydrogen peroxide and oxygen with a heavy metal-free catalyst. It is another aspect of the present invention to provide a method of synthesis of organic poly (disulfide) polymers that is not reliant on organic reaction media to proceed. Instead, the polymerization reactions proceed in aqueous media. It is still another aspect of the present invention to provide a method of synthesis of organic poly (disulfide) polymers that has the ability to polymerize a variety of dithiol monomers to high molecular weights. Possible monomers include, but are not limited to, aliphatic dithiols and alkoxy dithiols. The claimed method may also be applied to the polymerization of α,ω-dithiol prepolymers and oligomers. Additionally, it is an effective method for the formation of disulfide-crosslinked gels. Furthermore, fillers such as carbon may be added during the polymerization process.

In general, the present invention provides a method of synthesis of organic poly(disulfide) polymers, the method comprising providing a dithiol composition, and subjecting the dithiol composition to an oxidizing environment in the presence of a tertiary amine catalyst in an aqueous solution to provide a poly(disulfide) polymer. In one embodiment, the dithiol composition may comprise a dithiol compound selected from the group consisting of aliphatic dithiols and alkoxy dithiols. In another embodiment, the dithiol composition is a $C_2$-$C_{15}$ compound. In still another embodiment, the dithiol composition is selected from the group consisting of ethanedithiol, 2,2'-[ethane-1,2diylbis(oxy)]diethanethiol, α,ω-thiol functionalized tetraethylene glycol, α,ω-thiol functionalized poly(isobutylene), α,ω-thiol functionalized poly (ethylene glycol) and combinations thereof. In yet another embodiment, the dithiol composition comprises ethanedithiol, 2,2'-[ethane-1,2diylbis(oxy)]diethanethiol, or a combination thereof. In still another example of the method of the claimed invention, the oxidizing environment is provided by the presence of a peroxide such as hydrogen peroxide and atmospheric oxygen.

Optionally, the step of subjecting the dithiol composition to an oxidizing environment may take place in the additional presence of a solvent in which the hydrogen peroxide is immiscible. In one example, the solvent in which the hydrogen peroxide is immiscible is ethyl acetate. Additionally or in the alternative, the step of subjecting the dithiol composition to an oxidizing environment may additionally take place in the additional presence of a trithiol compound and results in a crosslinked poly(disulfide) polymer network. In one particular example, the trithiol compound is trimethylolpropane tris(3-mercaptopropionate).

Other optional components may also be present in any of the embodiments of the present invention. For example, a monothiol compound may be present during the step of subjecting the dithiol composition to an oxidizing environment. In one example, the monothiol compound may be cysteine. Additionally or in the alternative, a filler, such as carbon black, which becomes incorporated into the poly(disulfide) polymer, may be present during the step of subjecting the dithiol composition to an oxidizing environment.

The present invention also provides a poly(disulfide) polymer having a weight average molecular weight of greater than about 100,000 g/mol and a polydispersity index of about 2 or less. In one embodiment, the polydispersity index is less than or equal to about 1.8, 1.5 or even 1.35. The poly(disulfide) polymer may additionally comprise a filler incorporated therein. In one example, the filler is carbon black.

The present invention further provides a tetrathiol composition comprising a compound resulting from a reaction of a diacrylate with a trithiol compound. In such a tetrathiol composition, the diacrylate may be tetraethyleneglycol diacrylate and/or the trithiol compound may be trimethylolpropane tris (3-mercaptopropionate). A terathiol composition may be subjected to an oxidizing environment in the presence of a tertiary amine catalyst to provide a polytetrathiol polymer network.

DETAILED DESCRIPTION OF THE INVENTION

Figure 1A:
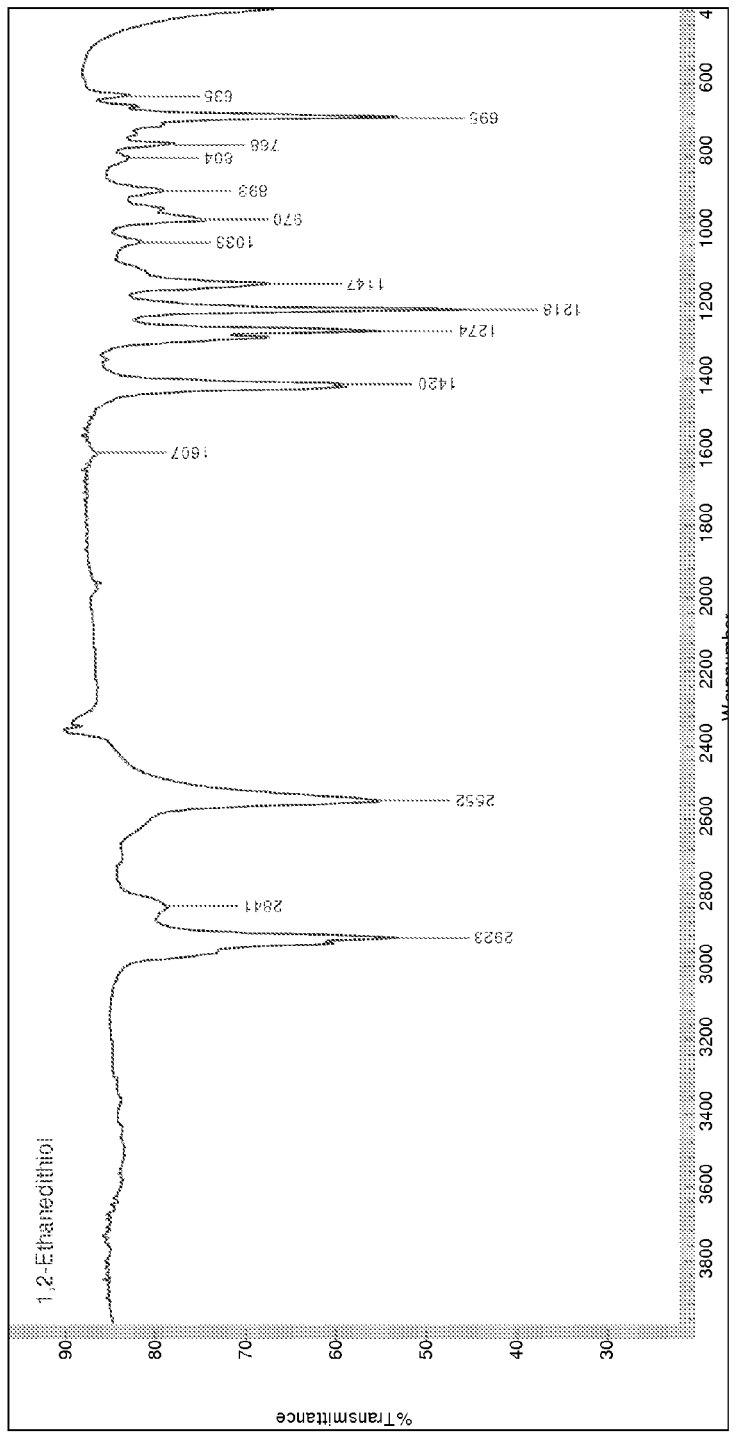
FIG. 1A is a Fourier Transform Infrared (FTIR) spectrum of 1,2-ethanedithiol monomer used in Example 1.

This invention relates to a new, environmentally friendly "green" method for the synthesis of poly(disulfide) polymers by an oxidative polymerization that utilizes a combination of atmospheric levels of oxygen, dilute hydrogen peroxide and triethylamine. The invention provides an environmentally friendly process to produce high molecular weight polymers ($M_n$=100,000 g/mol or more), and novel compositions of matter. The oxidation system is environmentally harmless and provides a work environment with reduced health risks. One half of the oxidizing system is atmospheric oxygen. Therefore the air used in the reaction may come directly from the atmosphere surrounding the reaction or from compressed air cylinders. The energy and cost of using pure oxygen is thereby negated. Cost savings may also be realized from the fact that the reaction is exothermic and does not require the application of heat to drive the reaction and therefore, may be conducted at ambient temperature (such as 25° C. for example). Also, the explosion and flammability hazards associated with pure oxygen use are foregone. The second half of the oxidizing system is also environmentally benign, as the decomposition products of hydrogen peroxide are water and oxygen. The dilute concentration (3%) of hydrogen peroxide used also diminishes the explosive and workers' health hazards associated with higher concentrations.

An additional advantage of the invention is the relatively short reaction time. While not wishing to condition patentability on any particular theory, it is believed that triethylamine catalyzes the oxidation reaction by abstracting or coordinating with the acidic sulfhydryl proton. The catalyst increases the rate of the reaction as well, and enables the production of high molecular weight product. Triethylamine is not a carcinogen, teratogen, or environmental toxin so the gels produced are suitable for biomedical applications.

The following examples are illustrative of the invention but should not be viewed as limiting the scope of the invention. The claims will serve to define the invention.

Fourier Transform Infrared (FTIR) spectroscopy (Digilab Excalibur Series FTS 3000) was used to analyze both the starting materials and final products. The starting material was sandwiched between two KBr crystals for analysis. Insoluble products were ground with KBr powder in a 1:100 ratio and then compressed into a solid pellet for analysis. Soluble products were dissolved in tetrahydrofuran solvent and cast onto a KBr crystal for analysis. Films were compression molded in a hydraulic Carver laboratory press. The powedered product was placed between two pieces of Krylon polyamide sheeting and subjected to 5000 psi and 160° C. for 10 minutes.

Differential scanning calorimetry, DSC, was carried out on a TA Q2000 DSC using a heat-cool-heat thermal cycle. A typical thermal cycle started by heating the sample from 40° C. to 175° C. at 10° C./min. The purpose of the first step is to remove any previous thermal history and is not shown in the DSC traces. In the second step of the cycle, the sample is cooled at 10° C./min to reach −80° C. The third step of the cycle heats the sample from −80° C. to 160° C. at 10° C./min.

Thermal gravimetric analysis (TGA) was performed on a TA 5000 TGA using a heating rate of 10° C./min from room temperature to 500° C. under nitrogen atmosphere. Analysis of the thermal data was performed in the Universal Analysis 2000 software that accompanies the instruments.

Soluble products were also analyzed by $^1$H and $^{13}$C using a Mercury 300 MHz nuclear magnetic resonance instrument. Analysis of the spectra was performed in 1D NMR Processor software produced by Advanced Chemistry Development.

Molecular weights of soluble products were determined by size exclusion chromatography (SEC) on a system equipped with six Waters Styragel® columns, a Waters 2487 Dual Absorbance UV detector, a Wyatt Optilab DSP Interferomatic Refractometer, a Wyatt DAWN EOS multi-angle laser light scattering detector and a Wyatte Viscostar viscometer. The data from the SEC was processed using Astra Version 5.3.4.14.

Example 1

Figure 1B:
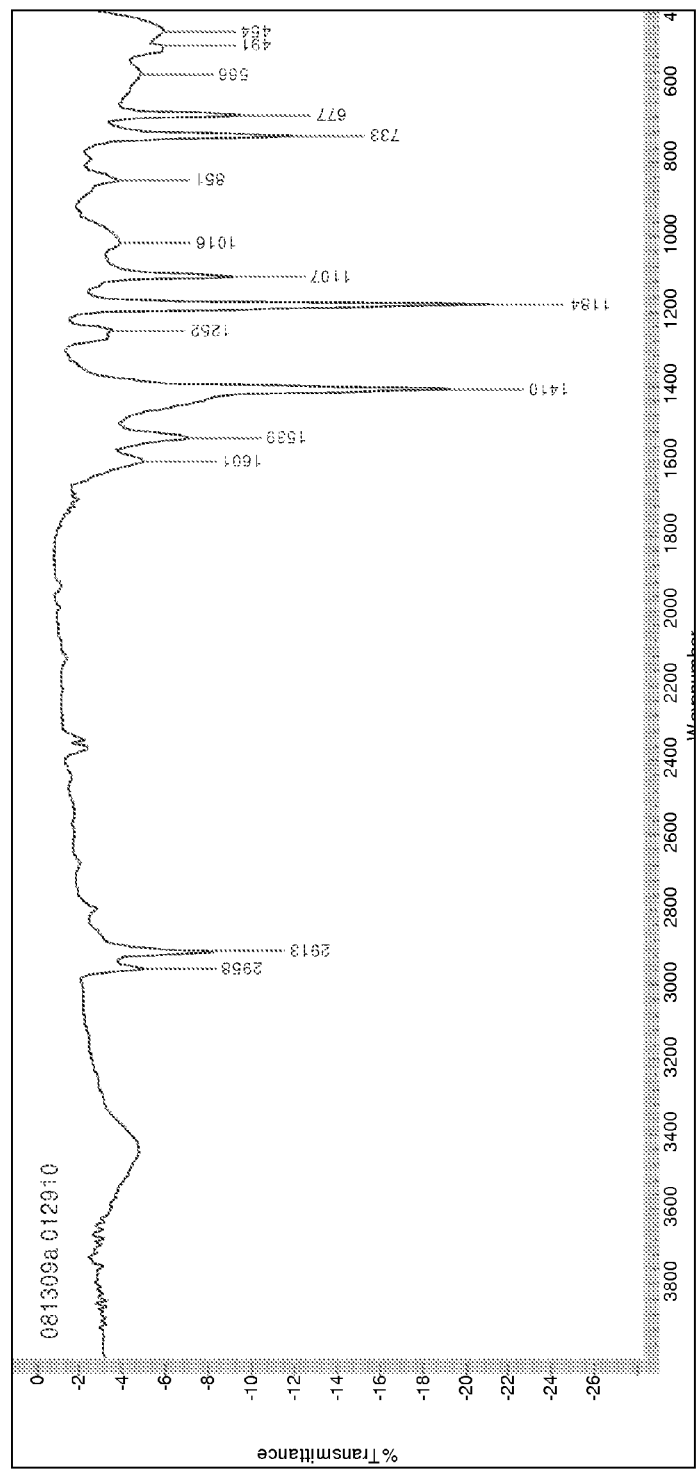
FIG. 1B is a FTIR) spectrum of the polymer product of Example 1, poly(ethanedisulfide).
Figure 1C:
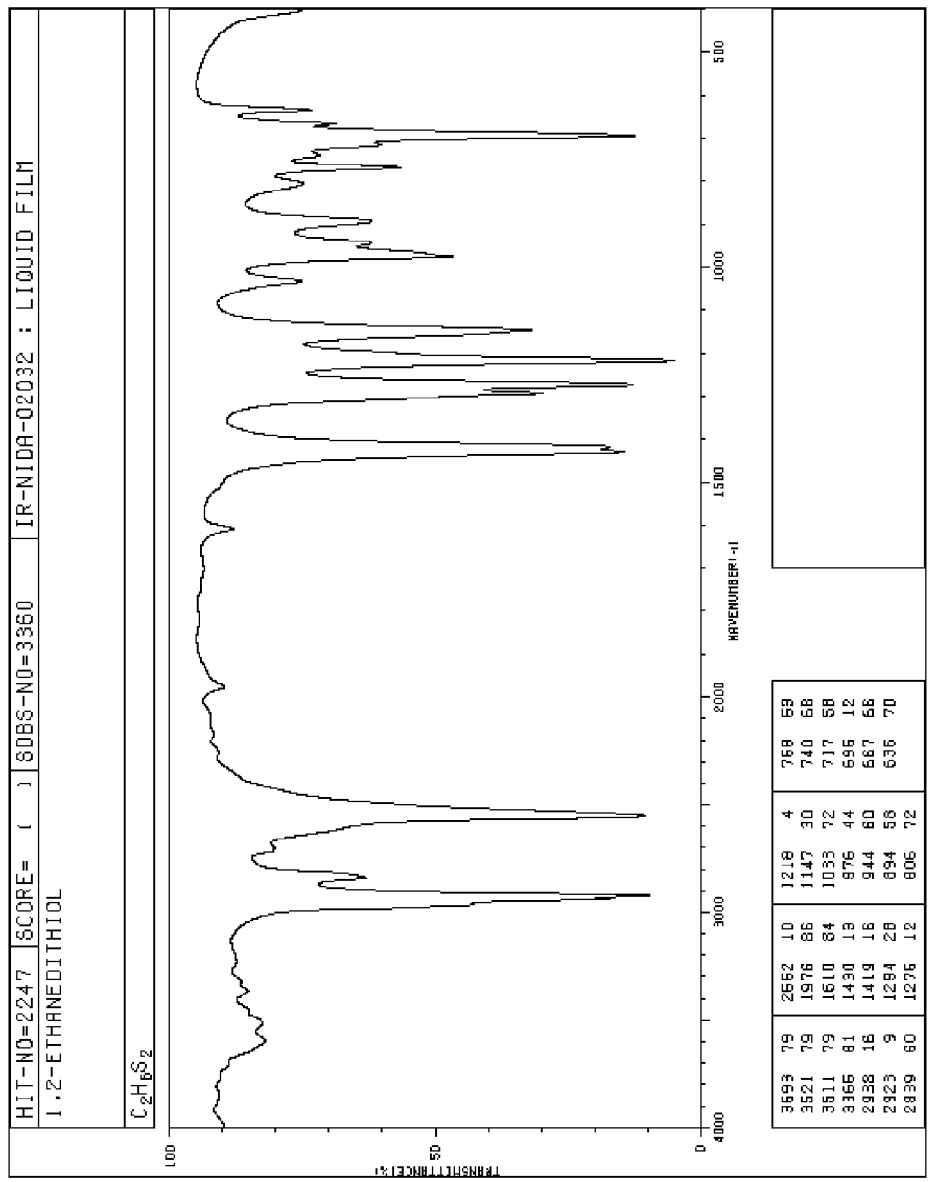
FIG. 1C is a reference FTIR spectrum of 1,2-ethanedithiol monomer.

Ethanedithiol ($C_2H_4(SH)_2$; 0.9 mL; 10.8 mmol; 0.12 mol/L (M)) and triethylamine ($N(CH_2CH_3)_3$; 3.1 mL; 22.2 mmol, 0.25M) were mixed for five minutes before being poured into a reaction flask filled with 8 mL hydrogen peroxide (8 mL of 3% aqueous solution; 7.0 mmol, 0.08M) and 80 mL phosphate buffer (pH=7.4). Air was bubbled into the bottom of the reaction flask for 30 minutes. The polymer was allowed to settle overnight before filtering and rinsing with deionized water. From the reaction, 0.8451 g of polymer was recovered to give an 83.6% conversion. The polymer is insoluble in common organic solvents (methanol, ethylacetate, tetrahydrofuran, dichloromethane, chloroform, dimethylsulfoxide, dimethylformamide, hexanes, dichlorobenzene, toluene etc). Its insolubility prevented analysis of the molecular weight. FIG. 1A shows the FTIR spectra of the starting material (1,2-ethanedithiol). FIG. 1B shows the FTIR spectra of the polymer product of Example 1. The FTIR spectrum of the monomer matches spectra found in the literature, and all critical peaks needed to identify the starting material ("1,2-Ethanedithiol." AIST:RIO-DB Spectral Database of Organic Compounds. On-line, Jan. 30, 2010. http://riodb01.ibase.aist.go.jp/sdbs/cgi-bin/direct_frame_top.cgi). The reference FTIR spectrum of 1,2-ethanedithiol is provided for comparison in FIG. 1C.

Two significant differences between the two spectra indicate clearly the formation of the polymeric product. The first indication is the disappearance of the strong peak at 2552 cm$^{-1}$ (FIG. 1A). The peak is believed to correspond to S—H stretching that is characteristic of terminal thiol groups (Thioplastics. *The Infrared Spectra Atlas of Monomers and Polymers*, Philadelphia, Pa.; Sadtler Research Laboratories, 1980, 262-266), and is not seen in the spectrum of the product. The second difference is the growth of signals at 491 cm$^{-1}$ and 454 cm$^{-1}$ in the spectra for the product (FIG. 1B) which are indications of S—S bonds. Because of their symmetry S—S bonds are inherently weak in infrared spectroscopy. The similarities between the spectra are also supportive of product formation because they demonstrate that many of the bonds found in the original monomer are still present in the polymer. The C—H stretching signals between 2800 cm$^{-1}$ and 3000 cm$^{-1}$ are present in both spectra. In the fingerprint region of the spectra, similar signals from C—C, C—H and C—S vibrational modes are seen with only minimal shifting after polymerization. For example the C—S signal seen at 695 cm$^{-1}$ shifts to 677 cm$^{-1}$ after the reaction. The shift is explained by the new environment of sulfur atom. In the polymer it is affected by a newly bonded sulfur atom where it used to be bonded to a hydrogen atom. The increases mass of the new substituent causes a shift wavelength of the C—S bond vibration.

Figure 2:
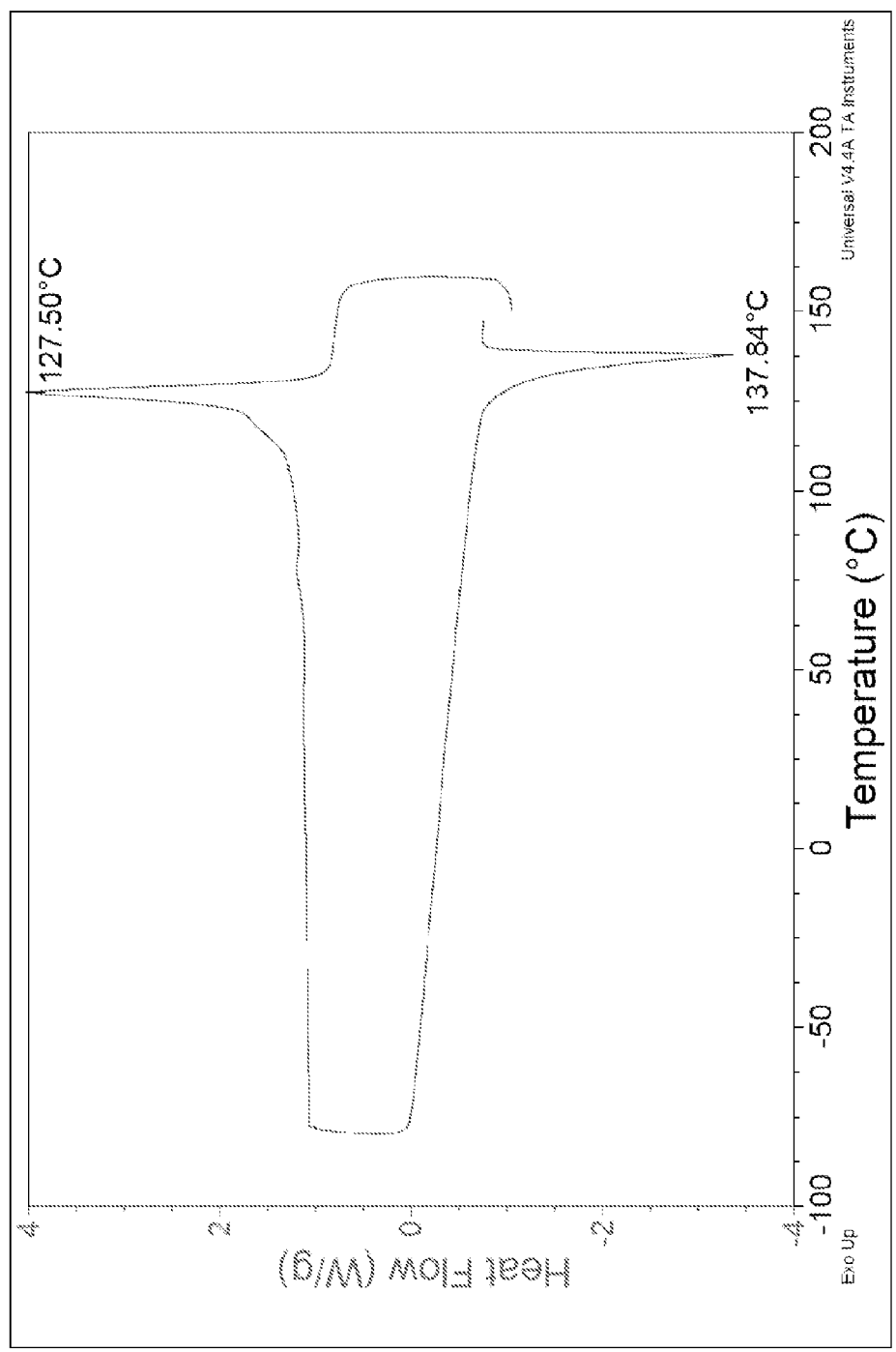
FIG. 2 is a Differential scanning calorimetry (DSC) plot of poly(ethanedisulfide) of Example 1.
Figure 3:
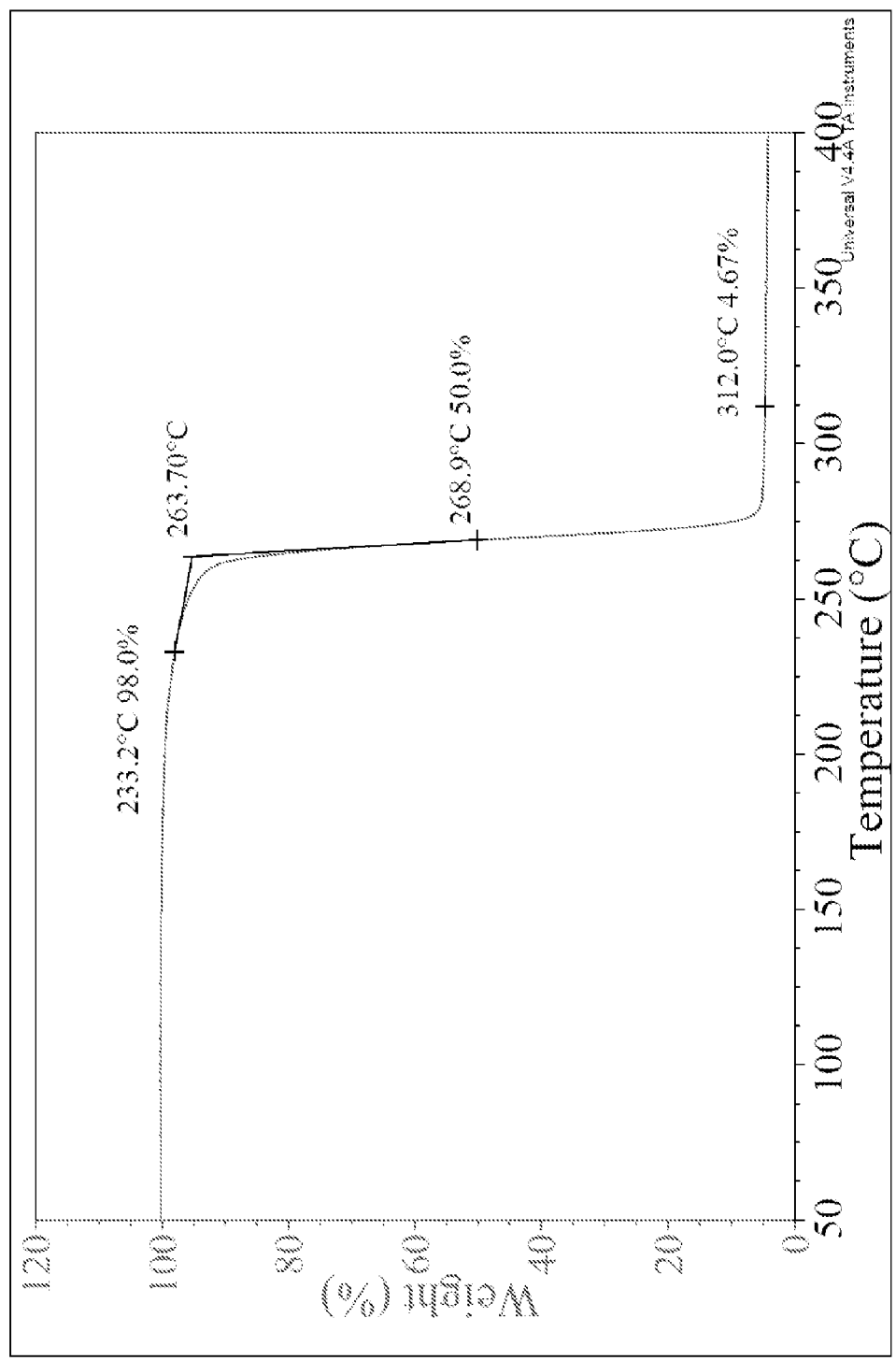
FIG. 3 is a Thermal Gravimetry Trace of poly(ethanedisulfide) of Example 1.

The results of thermal analysis are shown in FIGS. 2 and 3. FIG. 2 shows the DSC trace of the polymer product. The melting temperature of the polymer was 137.8° C. and the crystallization temperature was 127.5° C. The sharp endothermic and exothermic peaks indicate that the polymer is mostly crystalline. A slight shoulder can be seen in the crystallization curve that is no longer present upon heating. The shoulder may be attributed to a second crystalline or semicrystalline phase. During TGA, the polymer experiences 2% mass loss from decomposition at 233.2° C., at 268.9° C. the polymer is 50% decomposed and the thermal decomposition profile has reached a plateau at 312° C. The decomposition temperature, as determined by the Universal Analysis software was 263.7° C. and is indicated on FIG. 3.

Example 2

Figure 4:
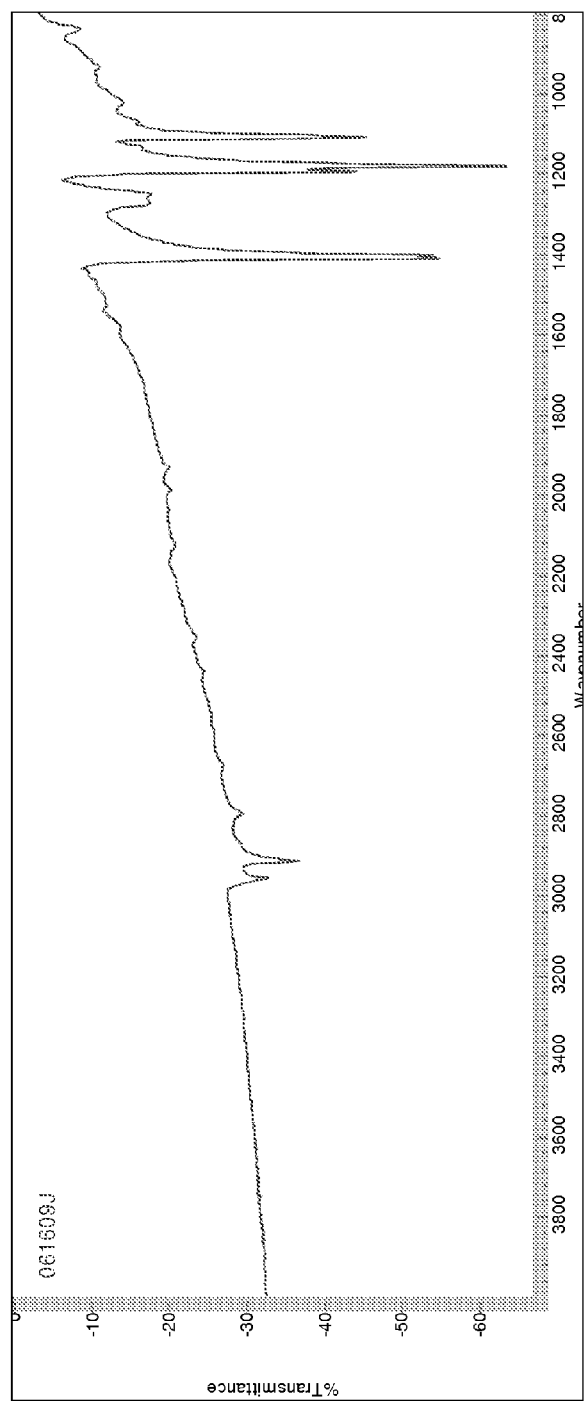
FIG. 4 is an FTIR Spectra of the product of Example 2.

Ethanedithiol (1.0 mL, 11.9 mmol, 0.60 mol/L (M)) was first mixed with triethylamine (4.98 mL, 35.7 mmol, 1.79M) and dilute aqueous hydrogen peroxide (14 mL of 3% aqueous solution, 12.32 mmol, 0.62M) was then added to the mixture while stirring. Air incorporation was achieved by agitation of the reaction flask. A polymer in the form of a fine white powder formed immediately upon the addition of hydrogen peroxide. The polymer was allowed 24 hours to flocculate before filtering and rinsing with cold water and cold methanol. The reaction produced 0.976 g of polymer to give a 86.9% conversion. The polymer is insoluble in common organic solvents (methanol, ethylacetate, tetrahydrofuran, dichloromethane, dimethylsulfoxide, dimethylformamide, hexanes, dichlorobenzene etc). Its insolubility prevented analysis of the molecular weight. The FTIR spectrum of the product is shown in FIG. 4 and is comparable to the spectrum from Example 1. Importantly, the spectrum does not display a signal in the range of 2550 cm$^{-1}$, which would indicate the presence of a thiol group. The angular baseline is attributed to drift in the instrument beam alignment.

Figure 5:
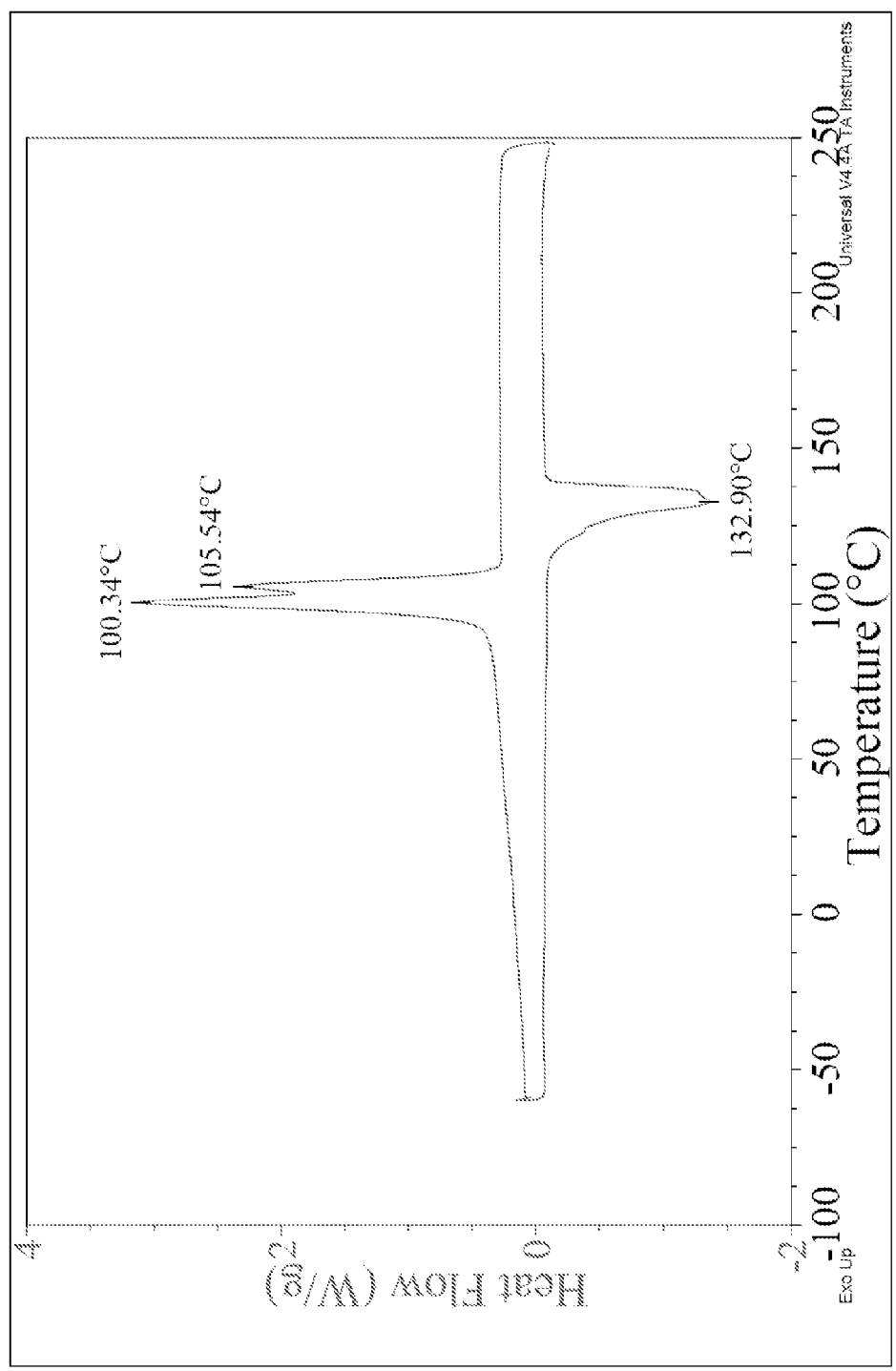
FIG. 5 is a DSC plot of the product of Example 2.
Figure 6:
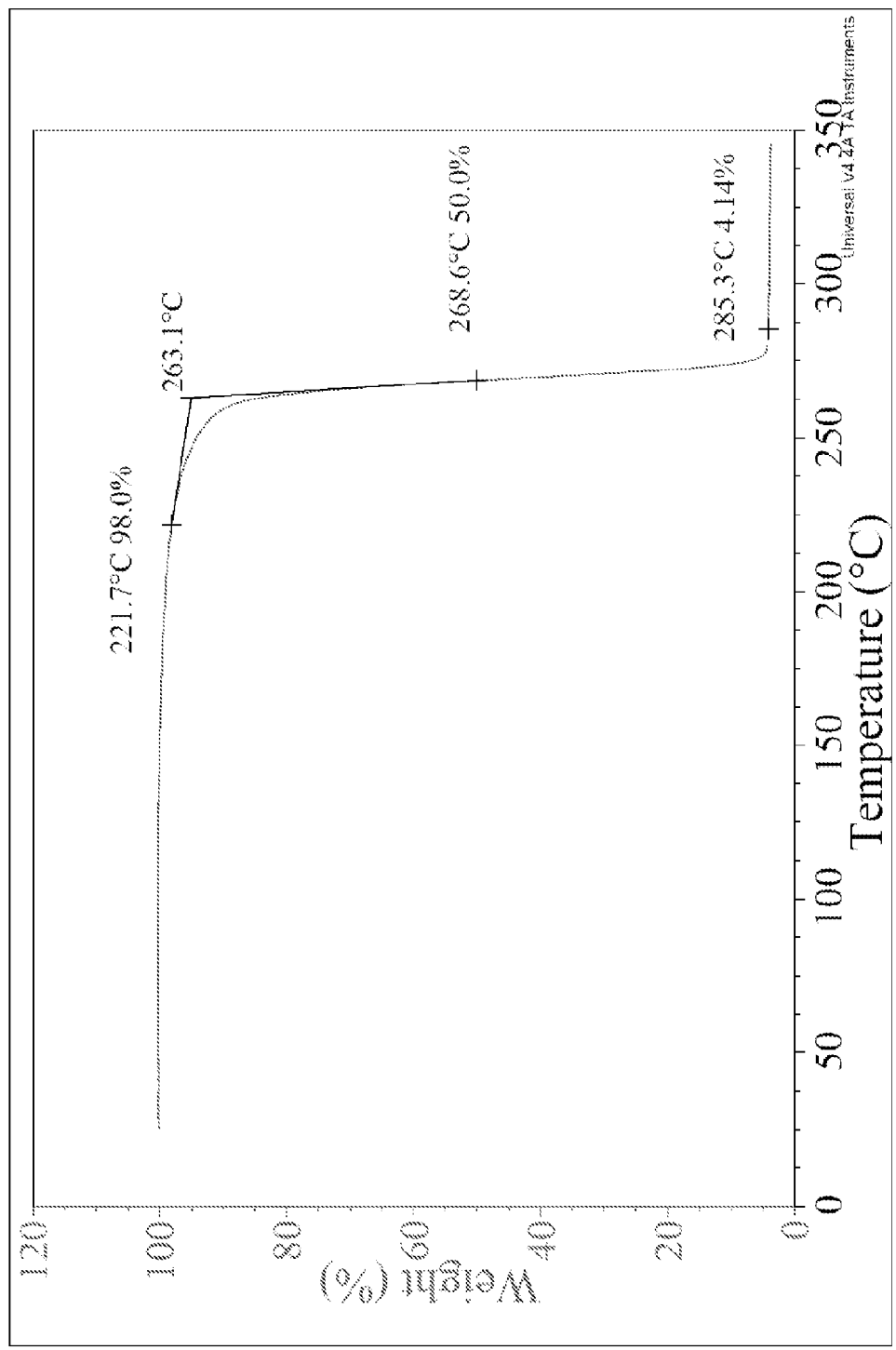
FIG. 6 is a Thermogravimetric Analysis (TGA) plot showing the percent weight loss versus temperature of product of Example 2.

The DSC plot for the polymer is shown in FIG. 5. Upon cooling, the crystallization peak shows two peaks, one at 105.54° C. and the other at 100.34° C. During the second heating ramp, only one peak at 132.90° C. is observed. The peak has a small shoulder, which, in combination with the crystallizing peaks is evidence that there are two different crystalline phases. During the TGA test, 2% mass loss was observed at 221.7° C., 50% mass loss was found at 268.6° C. and the end of thermal degradation was at 285.3° C. The degradation temperature as calculated by the Universal Analysis software was of 263.1° C. and is indicated on the TGA trace. The early onset of degradation also supports the presence of two fractions, or crystalline structures, with different thermal stability.

Figure 7:
FIG. 7 is a pair of photographs showing the poly(ethanedisulfide) of Example 2 before (left) and after (right) compression molding.
Figure 7:
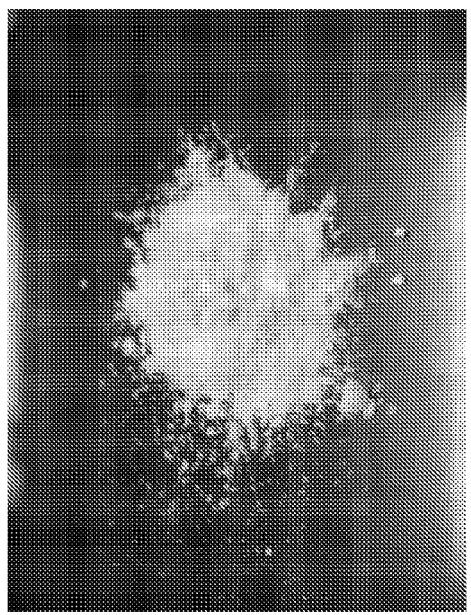

In FIG. 7, pictures of the polymer may be seen before and after compression molding. It can be seen that the polymer flows to form a thin, strong film. The film could be melted and reformed.

Example 3

Figure 8:
FIG. 8 is a chemical representation of 2,2'-[ethane-1,2diyl-bis(oxy)]diethanethiol.

In a round bottomed flask, 5.0 mL of 2,2'-[ethane-1,2diyl-bis(oxy)]diethanethiol (common name, 3,6-dioxa-1,8-octanedithiol, or DODT), the chemical structure of which is provided in FIG. 8, (30.5 mmol) was reacted with 13 mL triethylamine (93 mmol). About 8 mL of the stock solution was added to a reaction flask containing 60.0 mL hydrogen peroxide (60 mL of 3% aqueous solution; 52.8 mmol) and 60.0 mL deionized water. The resulting concentrations (in mol/L) of the reactants were as follows: 0.11M 2,2'-[ethane-1,2diylbis(oxy)]diethanethiol, 0.32M triethylamine, 0.41M hydrogen peroxide. Air was bubbled into the bottom of the reaction flask for 30 minutes. Polymer was gathered from sides of the reaction flask and from the solution which was allowed to settle overnight. Despite spilling some of the polymer solution during decanting, 2.0646 g of polymer was recovered to give 83.3% conversion. The dry product was a clear, rubbery polymer that was soluble in tetrahydrofuran and chloroform, but insoluble in hexanes or water. Although the structure resembles that of water-soluble triethylene glycol, neither the monomer nor polymer are soluble in water. The reaction may be summarized as follows:

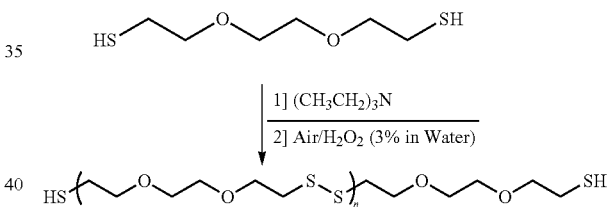

Figure 9A:
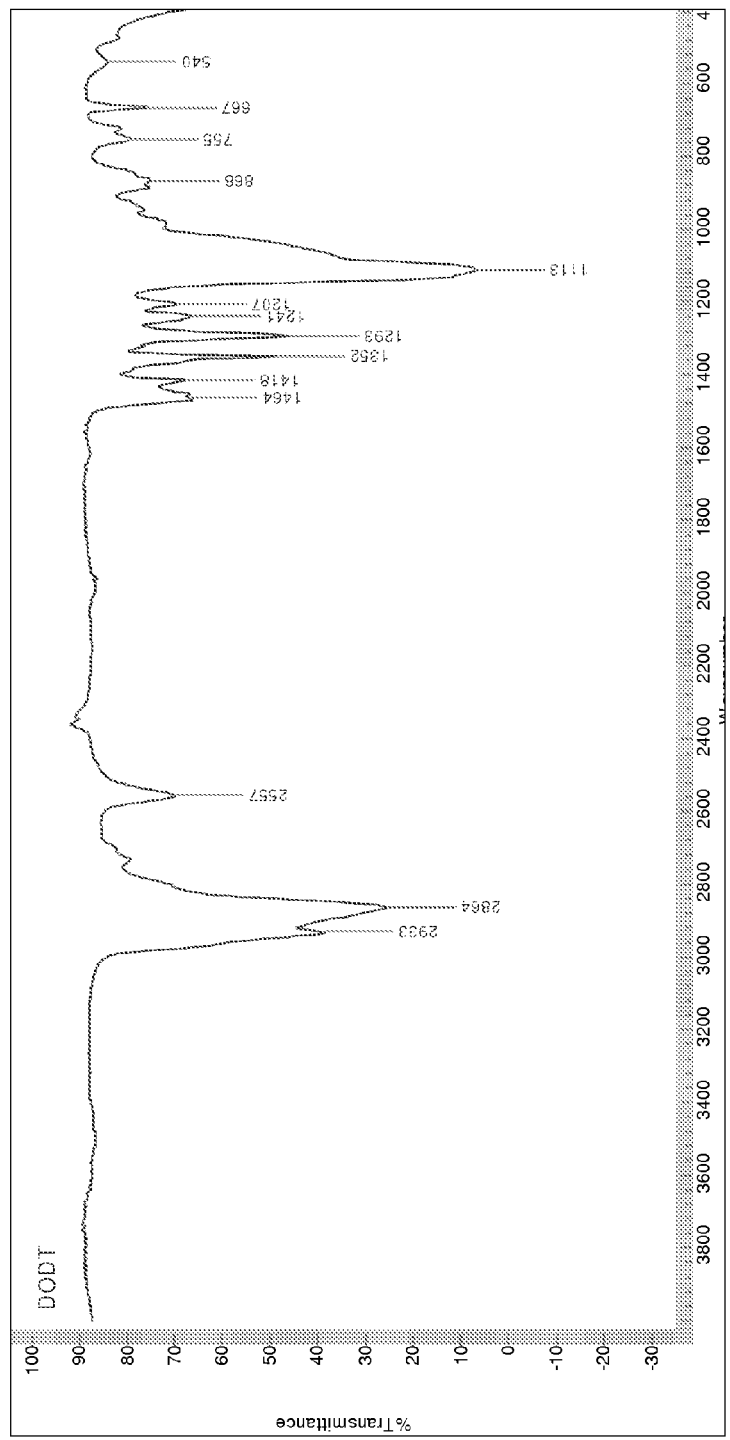
FIG. 9A is an FTIR spectrum of the monomer of Example 3.
Figure 9B:
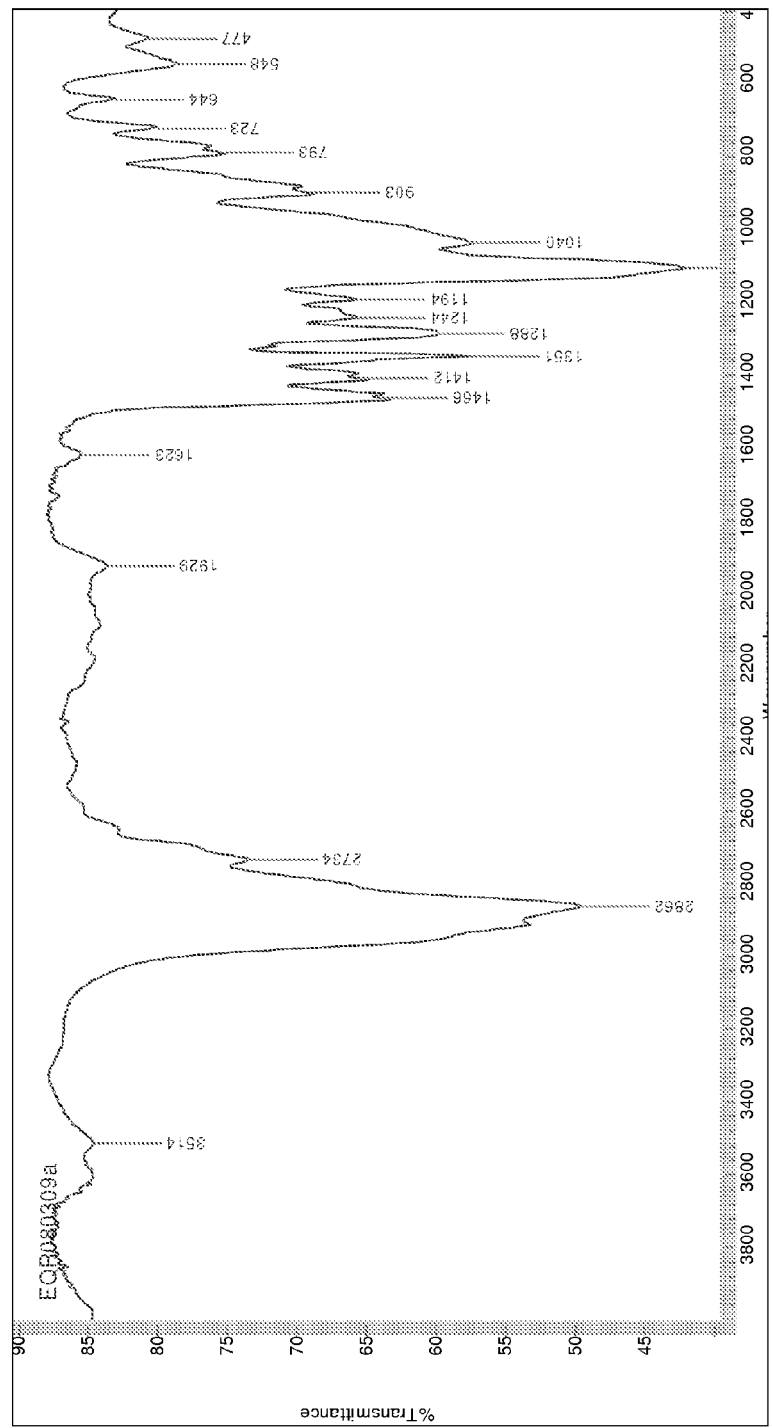
FIG. 9B is an FTIR spectrum of the polymer product of Example 3.

The infrared spectra of the starting material and of the polymer product are shown in FIGS. 9A and 9B, respectively. Two significant differences between the two spectra indicate clearly the formation of the polymeric product. The first indication is the disappearance of the strong peak at 2557 cm$^{-1}$ (FIG. 9A). The peak is believed to correspond to S—H stretching that is characteristic of terminal thiol groups (Thioplastics. *The Infrared Spectra Atlas of Monomers and Polymers*, Philadelphia, Pa.; Sadtler Research Laboratories, 1980, 262-266), and is not seen in the spectrum of the product. The second difference is the appearance of a signal at 477 cm$^{-1}$ which is believed to correspond to S—S bonds. Because of their symmetry, S—S bonds are inherently weak in infrared spectroscopy. The similarities between the spectra are also supportive of product formation because they demonstrate that many of the bonds found in the original monomer are still present in the polymer. The C—H stretching signals between 2800 cm$^{-1}$ and 3000 cm$^{-1}$ are present in both spectra. In the fingerprint region of the spectra, similar signals from C—C and C—H vibrational modes are seen with only minimal shifting after polymerization. For example, the C—S signal seen at 667 cm$^{-1}$ shifts to 644 cm$^{-1}$ after the reaction. The shift is explained by the new environment of carbon-bonded sulfur atom. It is now being affected by another sulfur atom rather than a hydrogen atom. Also, the signal at 1113 cm$^{-1}$ that represents C—O stretching is strong in both spectra indicating that the carbon-oxygen bonds have not been affected by the polymerization reaction.

Figure 10A:
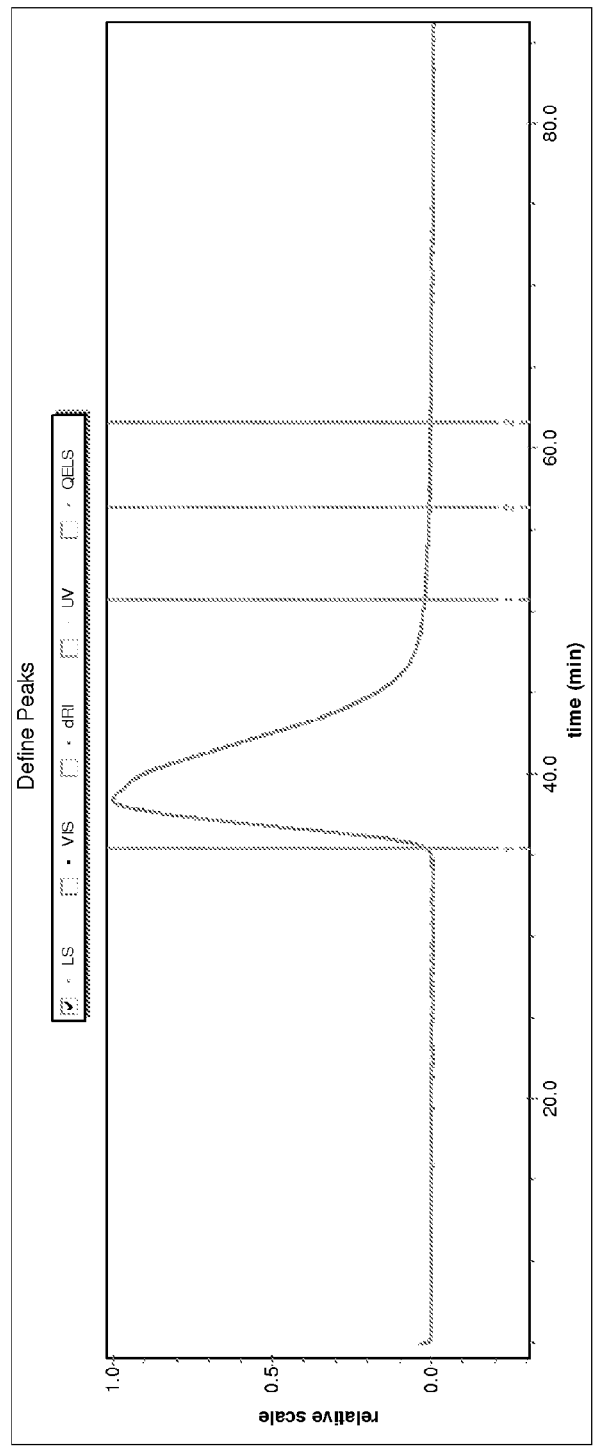
FIG. 10A shows the Multi-Angle Light Scattering Size Exclusion Chromatography (SEC) chromatogram for the polymer of Example 3.
Figure 10B:
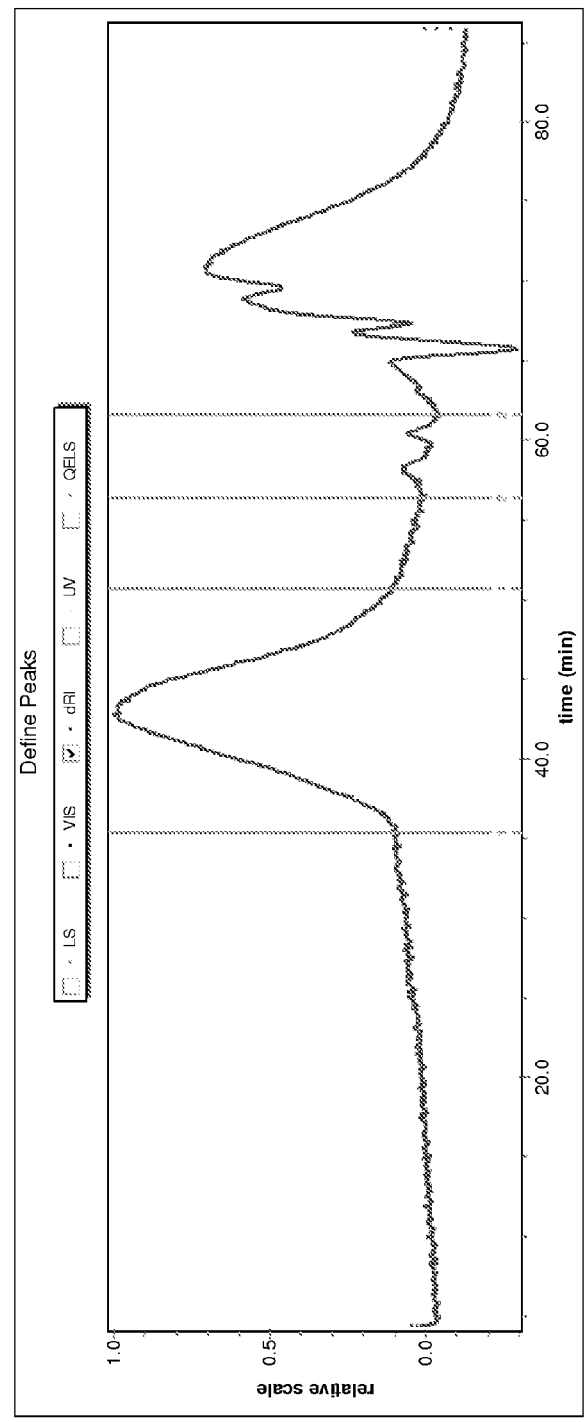
FIG. 10B shows the Refractive Index SEC chromatogram for the polymer of Example 3.
Figure 11:
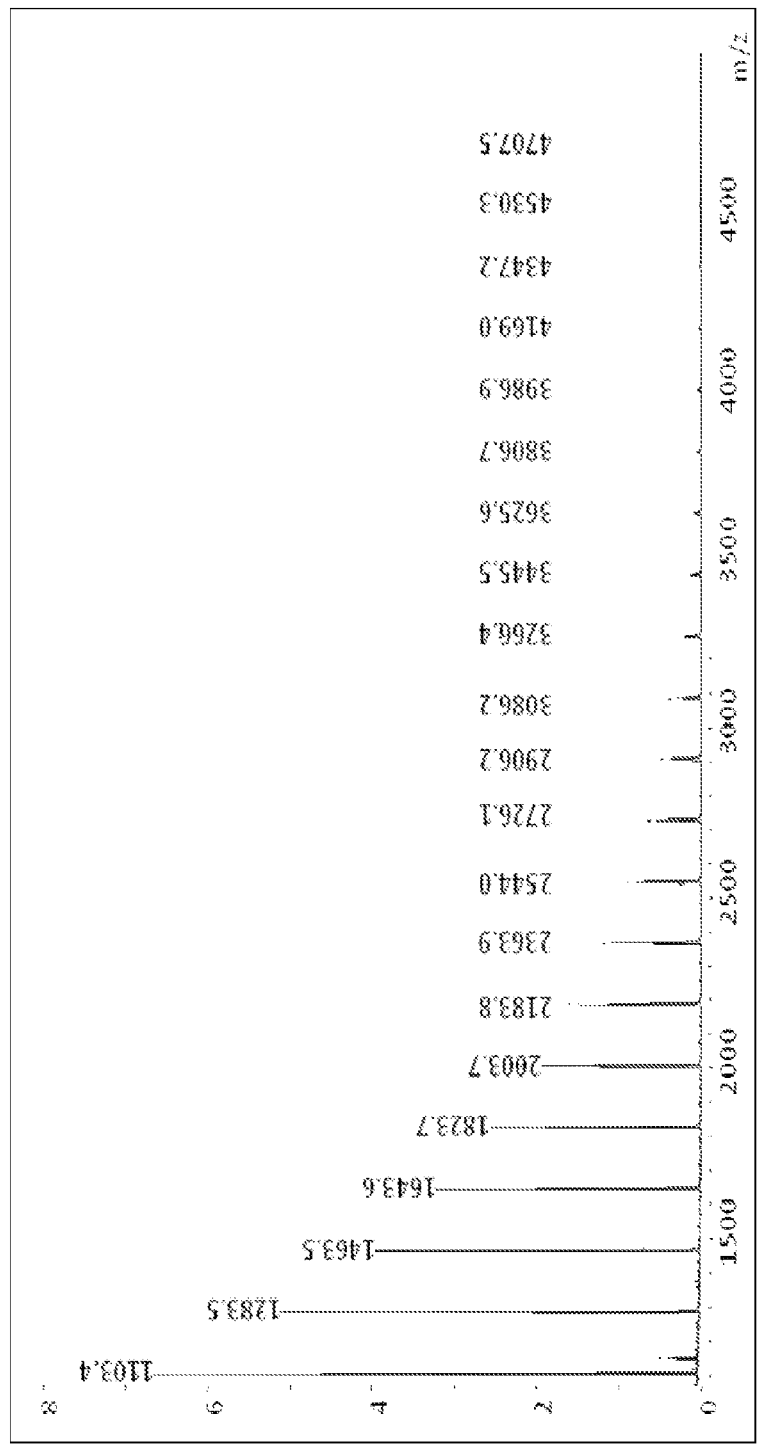
FIG. 11 is a Matrix-assisted laser desorption/ionization, time-of-flight (MALDI-ToF) spectrum for the polymer of Example 3.

FIGS. 10A and 10B shows two types of SEC traces (Multi-Angle Light Scattering (FIG. 10A) and Refractive Index (FIG. 10B)) for the polymer created in Example 3. Table 1 summarizes the data determined by SEC analysis. The main product has $M_n=9.03\times10^4$ g/mol, $M_w=2.41\times10^5$ g/mol and polydispersity index ($M_w/M_n$) of 2.66. The high molecular weight of the polymer prevented Matrix-assisted laser desorption/ionization, time-of-flight (MALDI-ToF) analysis of the main product but a small lower molecular weight fraction (seen in the RI SEC Trace, FIG. 10B) was available for MALDI-ToF analysis. The MALDI-ToF spectrum (FIG. 11) of the low molecular weight fraction ($M_n=4000$ g/mol) verified the repeat unit of the structure. The peaks in the mass spectrum are at 180 m/z intervals indicating that the repeat unit of the polymer has a mass of 180 g/mol. This mass, 180 g/mol, directly correlates with the predicted repeat unit of the polymer which has a mass of 180 g/mol. Analysis of the MALDI spectrum also indicated the absence of end groups in low molecular weight fraction. Thus it is concluded that the low molecular weight fraction is cyclic.

TABLE 1

Data from Size Exclusion Chromatography

| Molecular Weights: | |
| --- | --- |
| Number Average ($M_n$) | $9.03 \times 10^4$ (g/mol) |
| Weight Average ($M_w$) | $2.41 \times 10^5$ (g/mol) |
| Polydispersity Index ($M_w/M_n$) | 2.66 |
| Hydrodynamic Radius [$R_h(z)$] | 18.6 (nm) |
| Viscosity [$\eta(z)$] | 70.3 (mL/g) | dn/dc based on 100% mass recovery: 0.124 (mL/g)

Figure 12A:
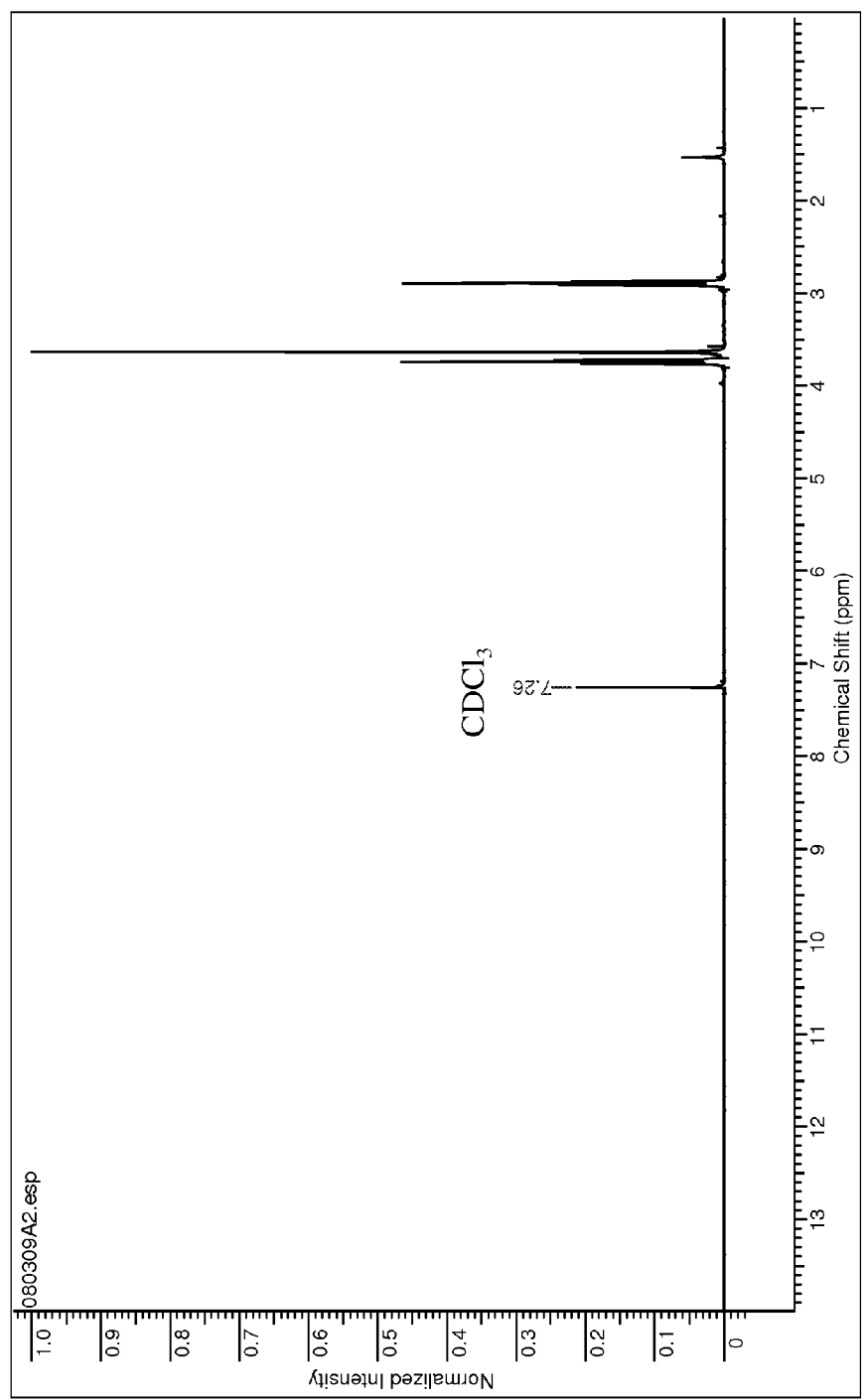
FIG. 12A is a proton Nuclear Magnetic resonance (NMR) spectrum of the polymer of Example 3.
Figure 12B:
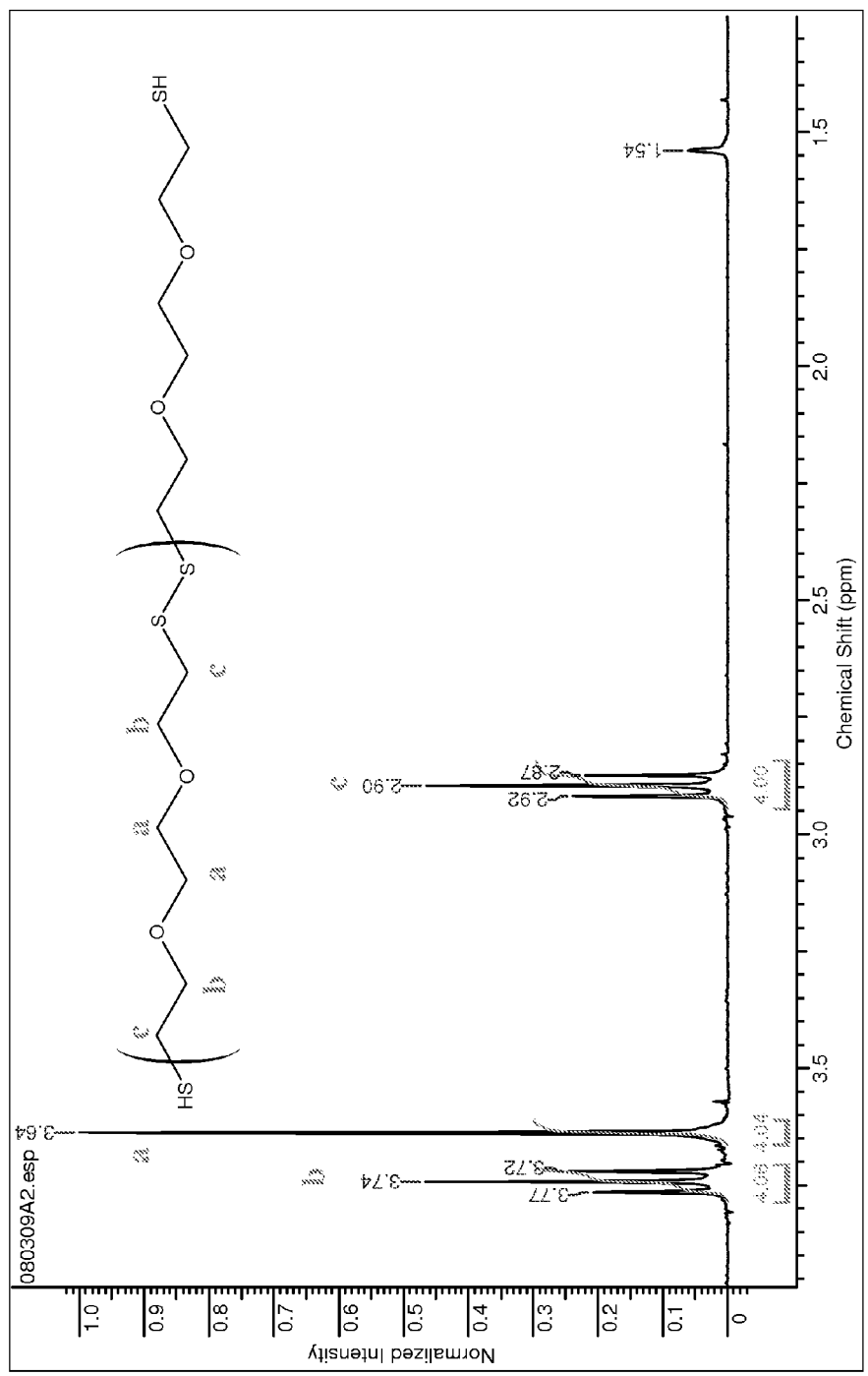
FIG. 12B is a labeled enlargement of the peaks of the NMR spectrum of FIG. 12A.
Figure 12C:
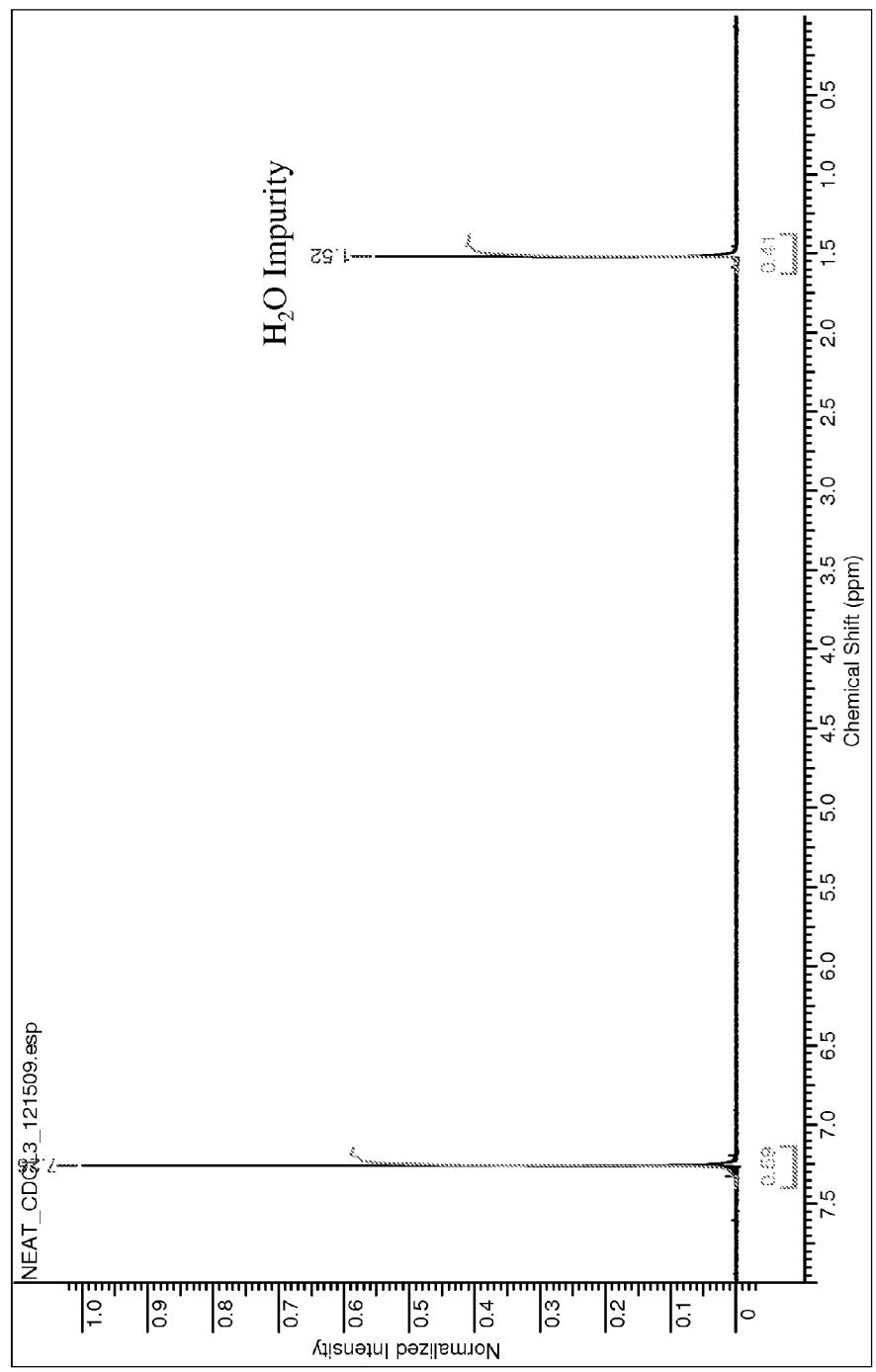
FIG. 12C is a proton NMR spectrum of deuterated solvent.

FIG. 12A shows the full proton NMR spectrum of the polymer product and FIG. 12B provides a labeled detail of the peaks shown in FIG. 12A that includes their integration values. In the proton NMR spectrum, the triplet peaks at 3.74 ppm and 2.90 ppm are assigned to the protons on oxygen-adjacent carbons and sulfur-adjacent carbons respectively. The singlet peak at 3.64 ppm represents the four equivalent protons found on the two central carbon atoms of the monomer. The integration values match the expected values since each monomer contains four of each type of proton. The small peak 1.54 ppm is not included in the integration because it is a combination of thiol protons from the low molecular weight fraction of the polymer and residual water found in the polymer and deuterated chloroform solvent. A proton NMR spectrum of the neat deuterated solvent is shown in FIG. 12C for comparison and clearly indicates the presence of water impurity.

Figure 13A:
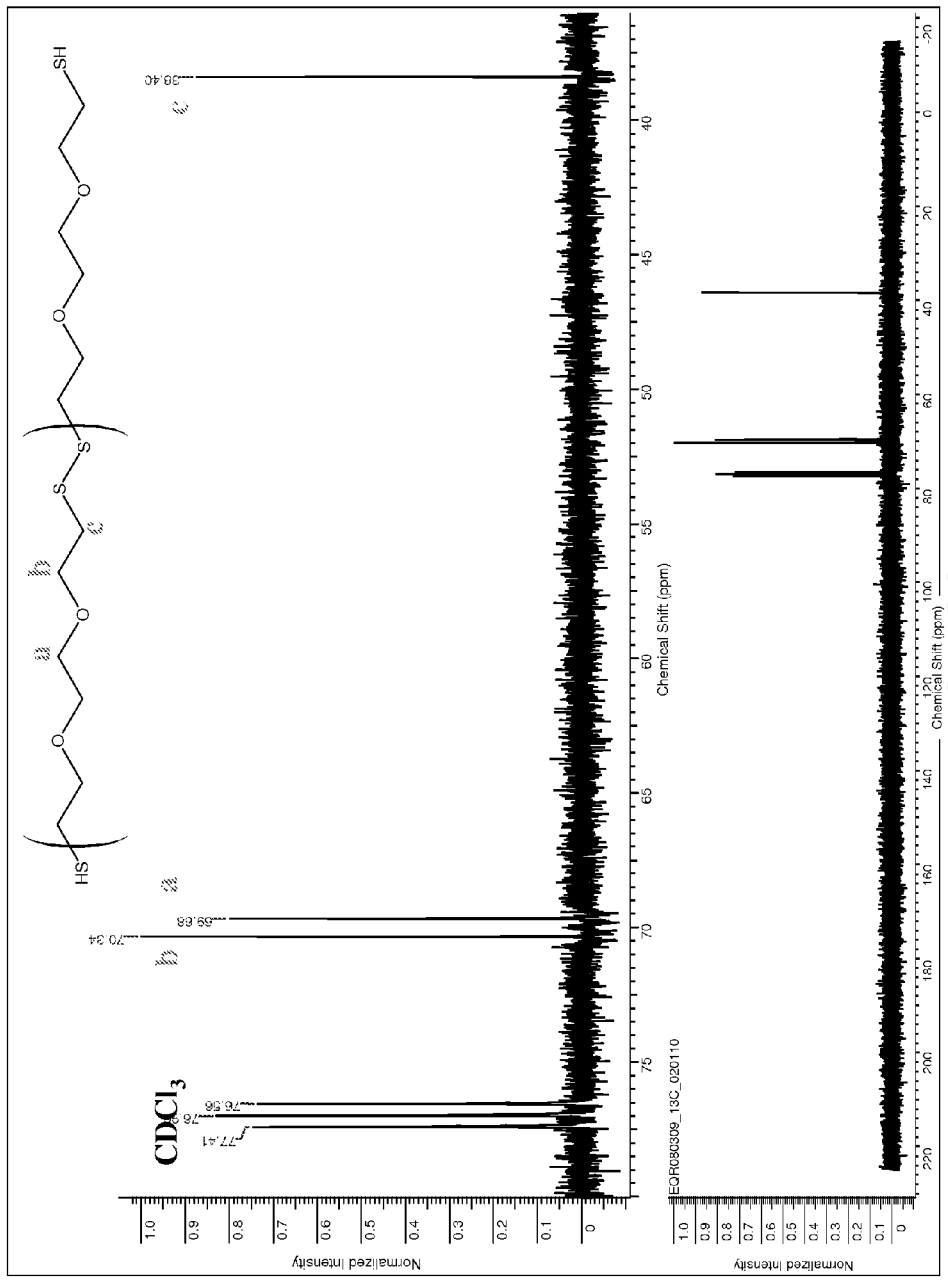
FIG. 13A is a $^{13}C$ NMR spectrum of the polymer of Example 3.
Figure 13B:
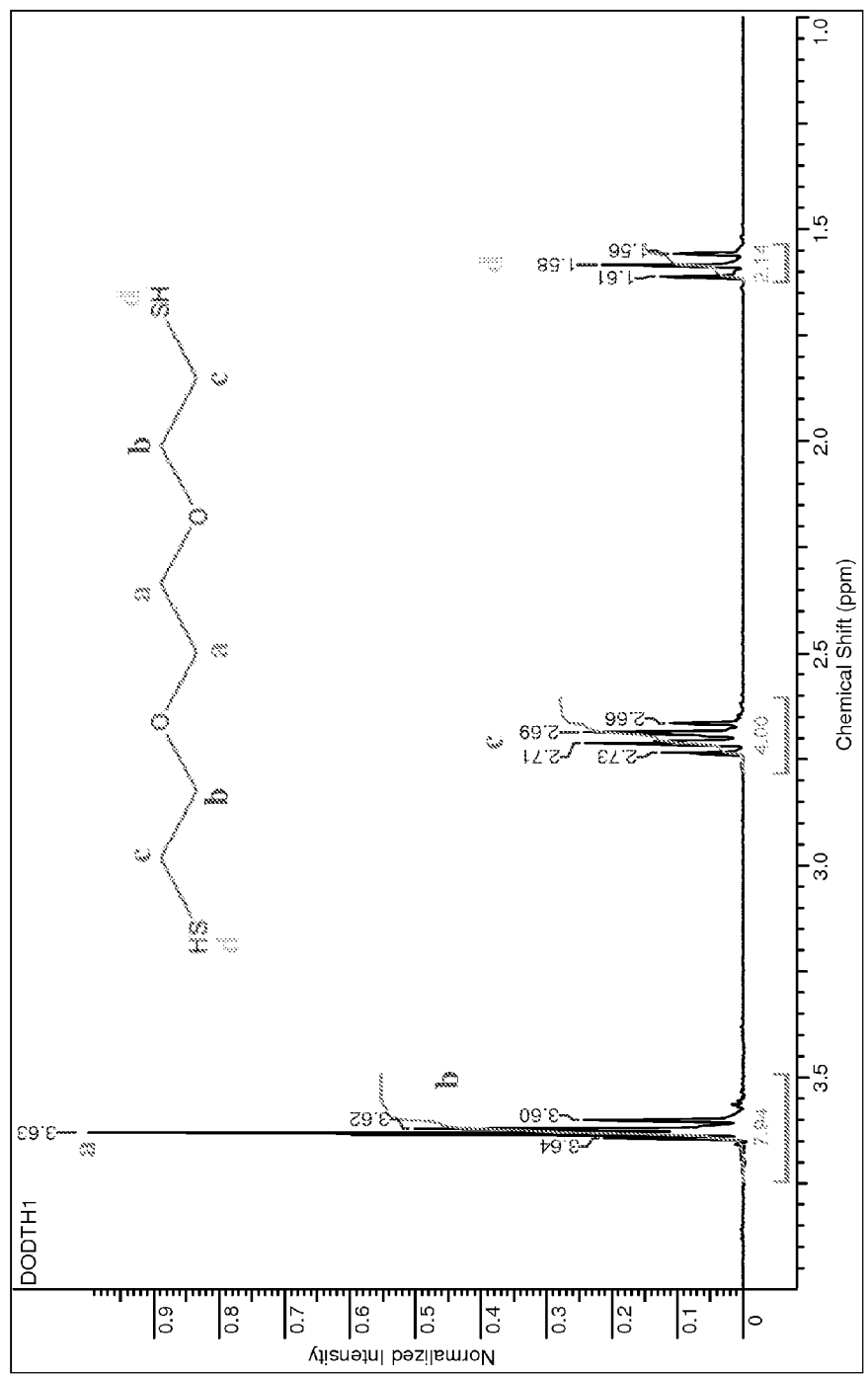
FIG. 13B is a $^1H$ NMR spectrum of the DODT starting material of Example 3.
Figure 13C:
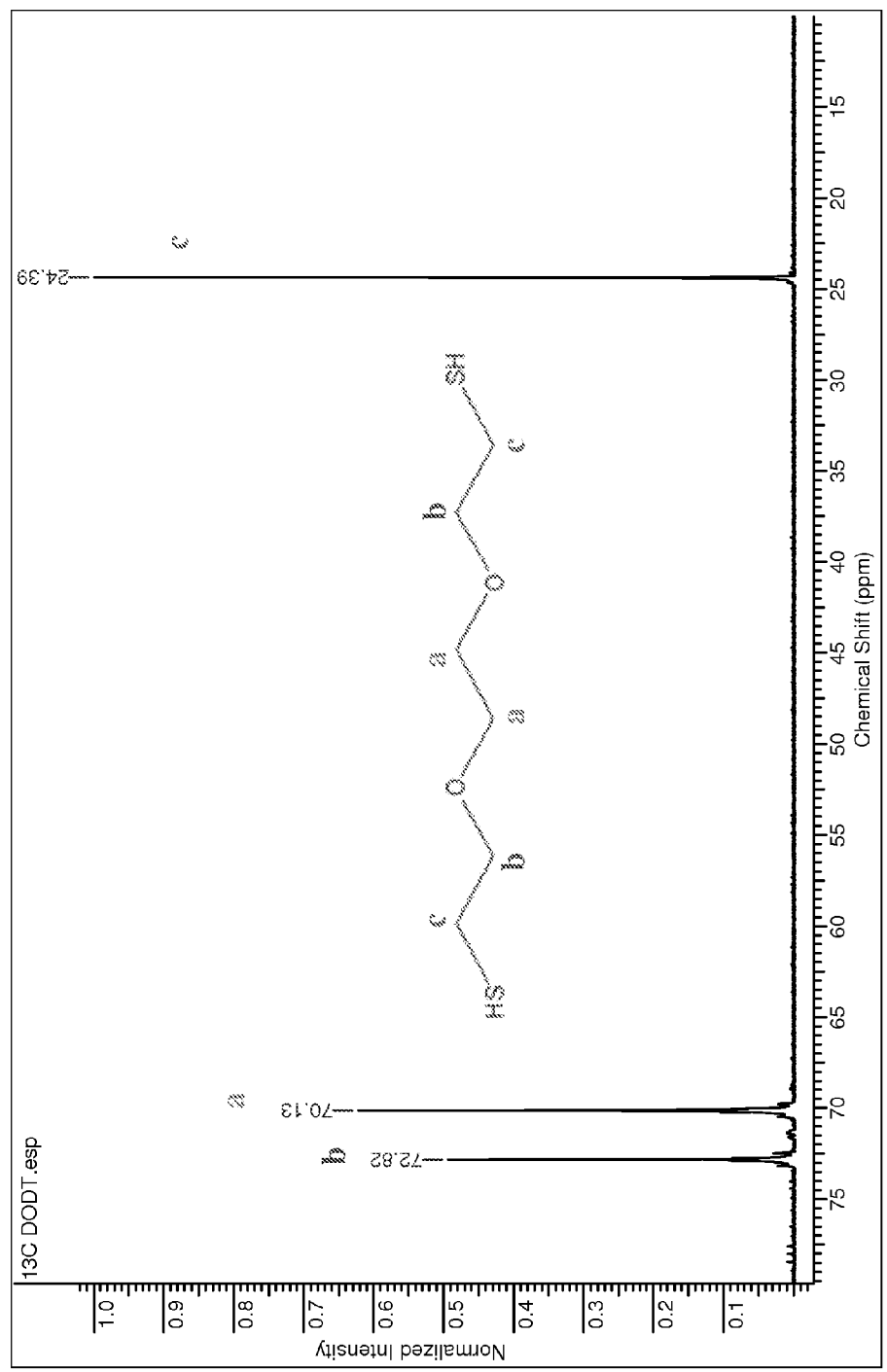
FIG. 13C is a $^{13}$C NMR spectrum of the DODT starting material of Example 3.

The $^{13}$C NMR spectrum (FIG. 13A) shows three peaks from the polymer product. It also shows three peaks from the deuterated chloroform solvent at 76 ppm which is expected. The peak at 69.68 ppm corresponds to the two carbon atoms at the center of the monomer. The peak at 70.35 ppm corresponds to the oxygen-adjacent carbons and the peak at 38.46 corresponds to the sulfur-adjacent carbons in the monomer. Because of the high molecular weight of the polymer, signals from end-group carbon atoms cannot be detected. The proton and carbon NMR spectra for the starting material are available for comparison in FIGS. 13B and 13C, respectively.

Figure 14:
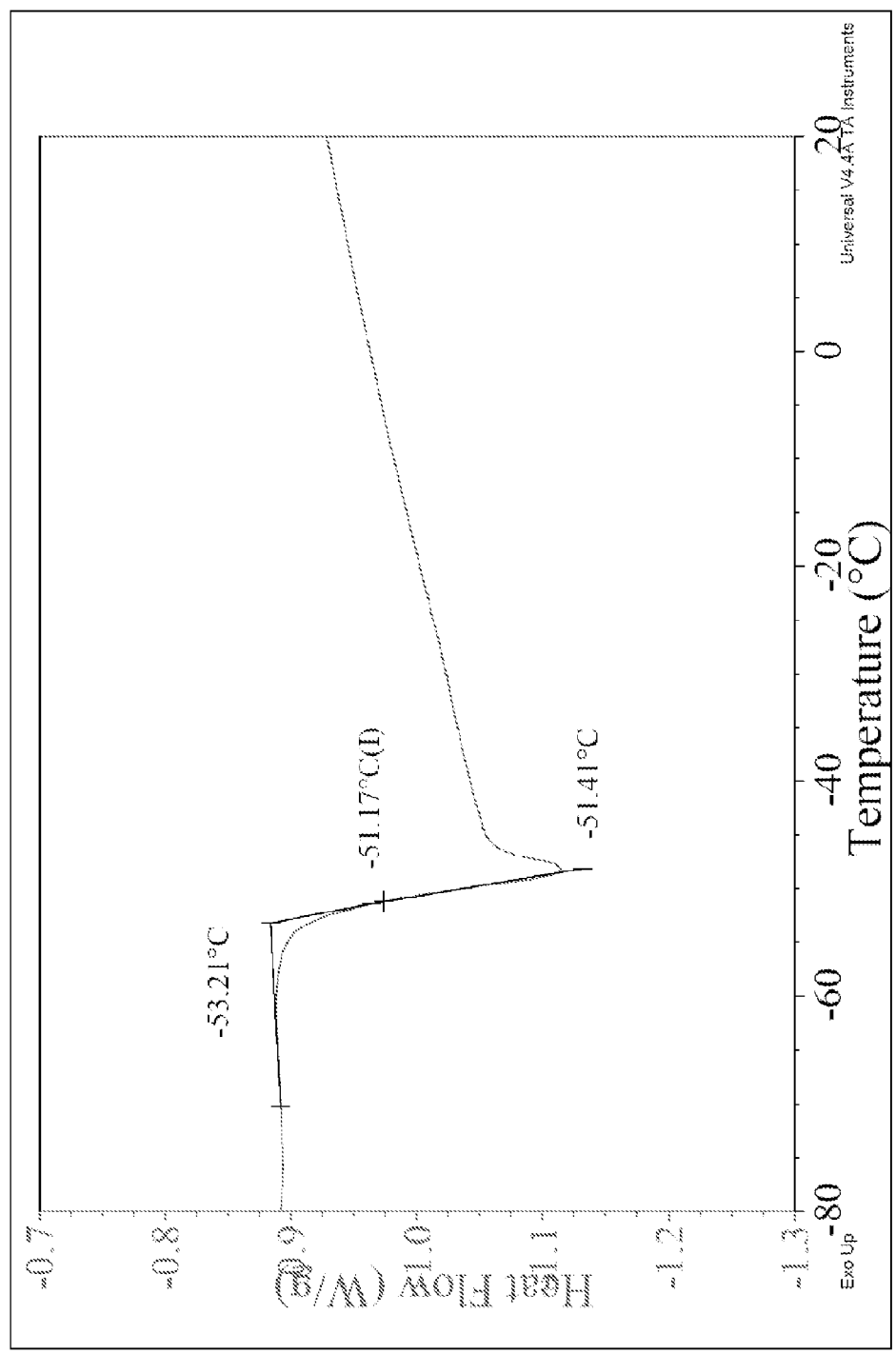
FIG. 14 is a DSC plot of the product of Example 3.
Figure 15:
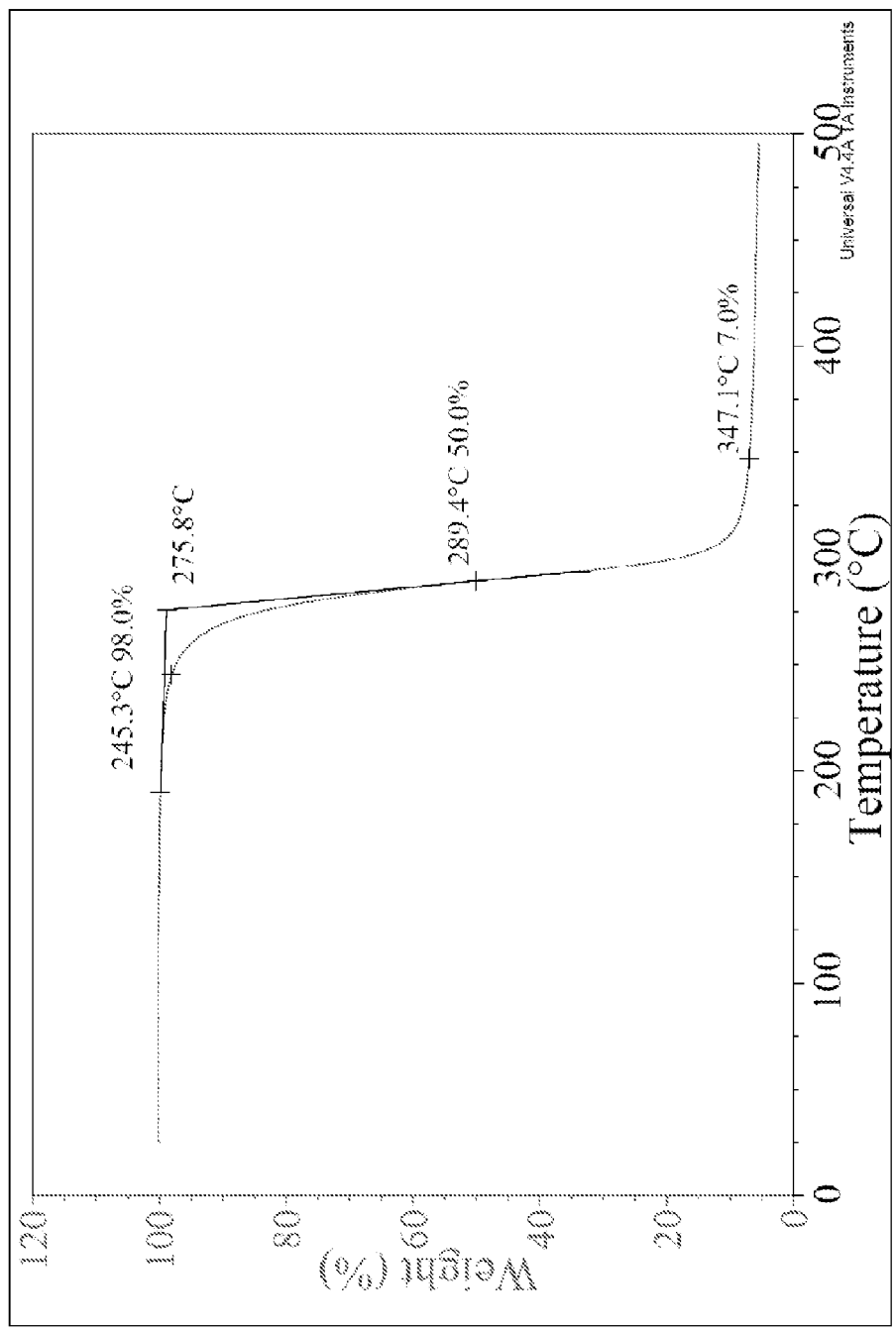
FIG. 15 is a TGA plot for the product of Example 3.
Figure 16:
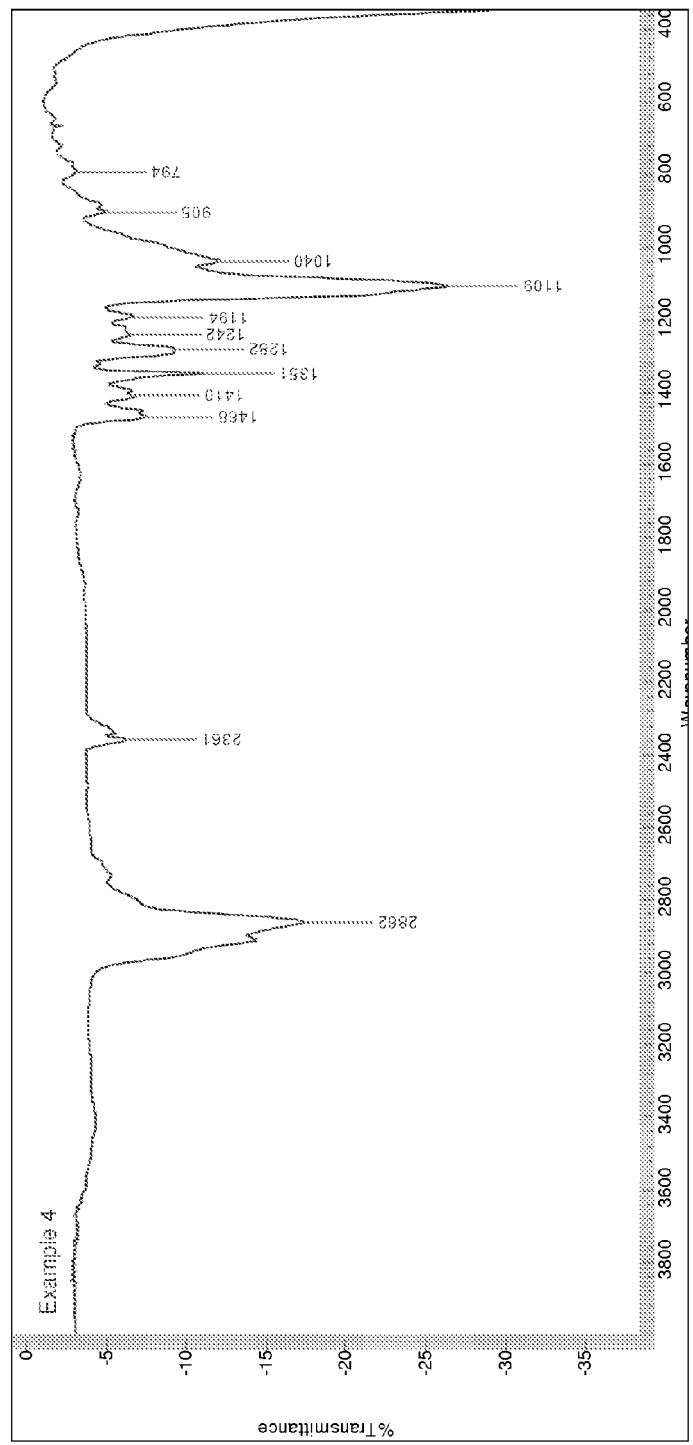
FIG. 16 is an FTIR Spectra of the product of Example 4.

Analysis by DSC showed only one, low-temperature, transition with no crystalline melting peak, indicating that the polymer is amorphous. The glass transition temperature, as shown in FIG. 14, appears from −53.21° C. to −51.41° C. No transition was found above 20° C. The TGA trace (FIG. 15) shows that the polymer has lost 2% of its initial mass by 245.3° C., 50% mass loss has been achieved by 289.4° C. and the decomposition profile has reached a plateau by 347.1° C. The decomposition temperature as calculated by the Universal Analysis software is 275.8° C. and is indicated in the figure.

Example 4

2,2'-[ethane-1,2diylbis(oxy)]diethanethiol (1.00 mL; 6.1 mmol; 0.31M) was reacted with triethylamine (2.55 mL; 18.3 mmol; 0.94M) for one hour before dilute aqueous hydrogen peroxide was added in 1 mL aliquots (16 mL of 3% aqueous solution; 14.1 mmol; 0.72M) while stirring. Air incorporation was achieved by agitation of the reaction flask for 5 minutes. The reaction flask was left open to the atmosphere for 20 hours, after which the aqueous portion was decanted. The product was rinsed with water and methanol and allowed to soak in acetone. Excess acetone was decanted and the polymer was placed in a vacuum oven until dry. The reaction produced 1.0288 g of rubbery polymer to give a 92.4% conversion.

The FTIR spectrum of the product formed in Example 4 very similar to the FTIR spectrum for Example 3, FIG. 9B. The critical indicator of polymer formation is that the spectrum shows no thiol peak at 2550 cm$^{-1}$.

Figure 17A:
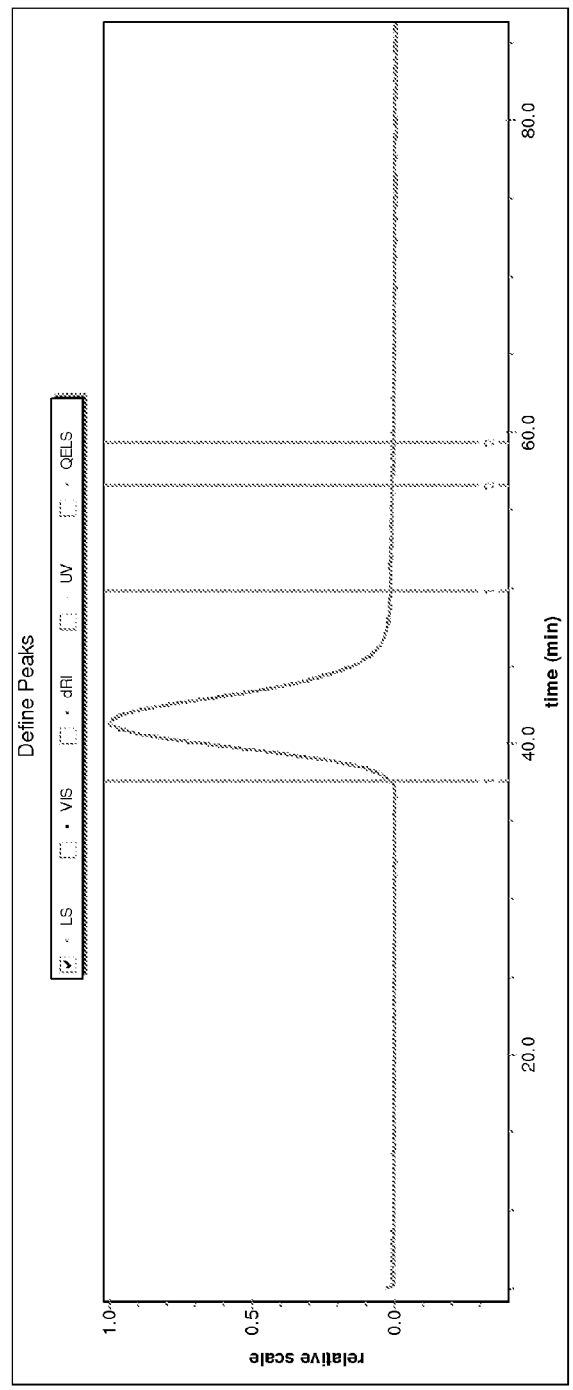
FIG. 17A shows the light scattering SEC chromatogram of the product of Example 4.
Figure 17B:
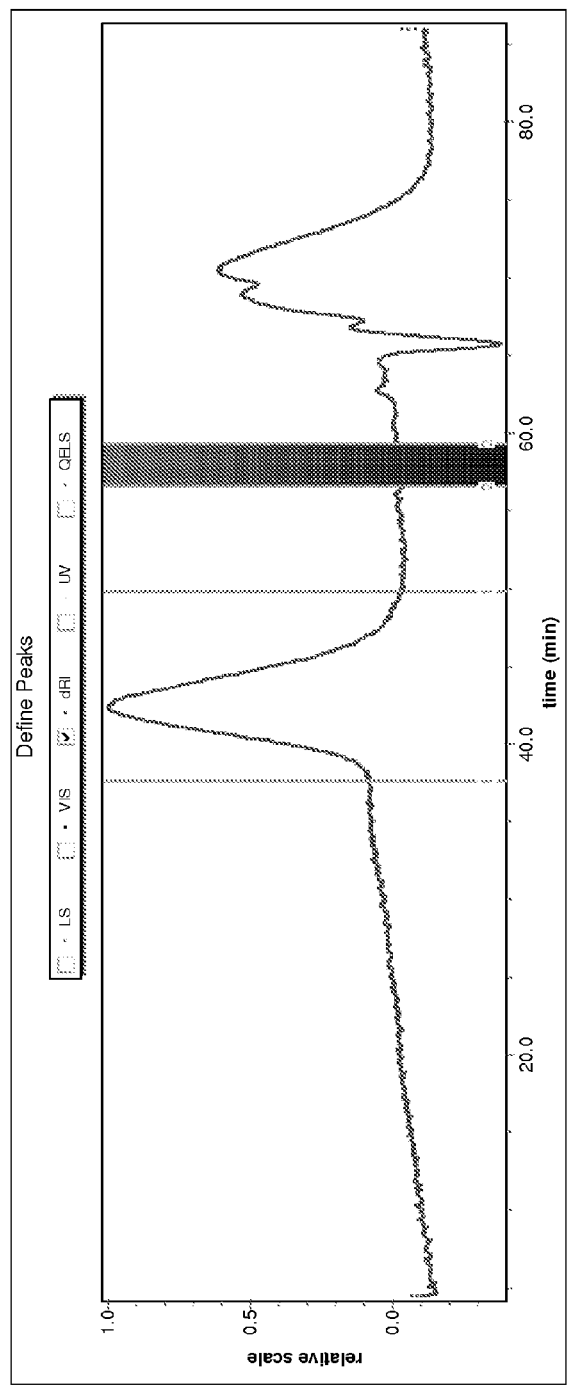
FIG. 17B shows the refractive index SEC chromatogram of the product of Example 4.

FIGS. 17A and 17B show the Light Scattering and Refractive Index SEC traces, respectively, of the product of Example 4, and Table 2 summarizes the data. The main peak has a very similar molecular weight to Example 3. There is again a small peak separate from the main high molecular weight peak that indicates the presence of a lower molecular weight fraction.

TABLE 2

Data from Size Exclusion Chromatography

| | Peak 1 |
| --- | --- |
| Molecular Weights: | |
| Number Average ($M_n$) | $9.775 \times 10^4$ (g/mol) |
| Weight Average ($M_w$) | $1.421 \times 10^5$ (g/mol) |
| Polydispersity Index ($M_w/M_n$) | 1.45 |
| Hydrodynamic Radius [$R_h(z)$] | 12.5 (nm) |
| Viscosity [$\eta(z)$] | 71.3 (mL/g) | dn/dc based on 100% mass recovery of Peak 1: 0.126 (mL/g)

Figure 18:
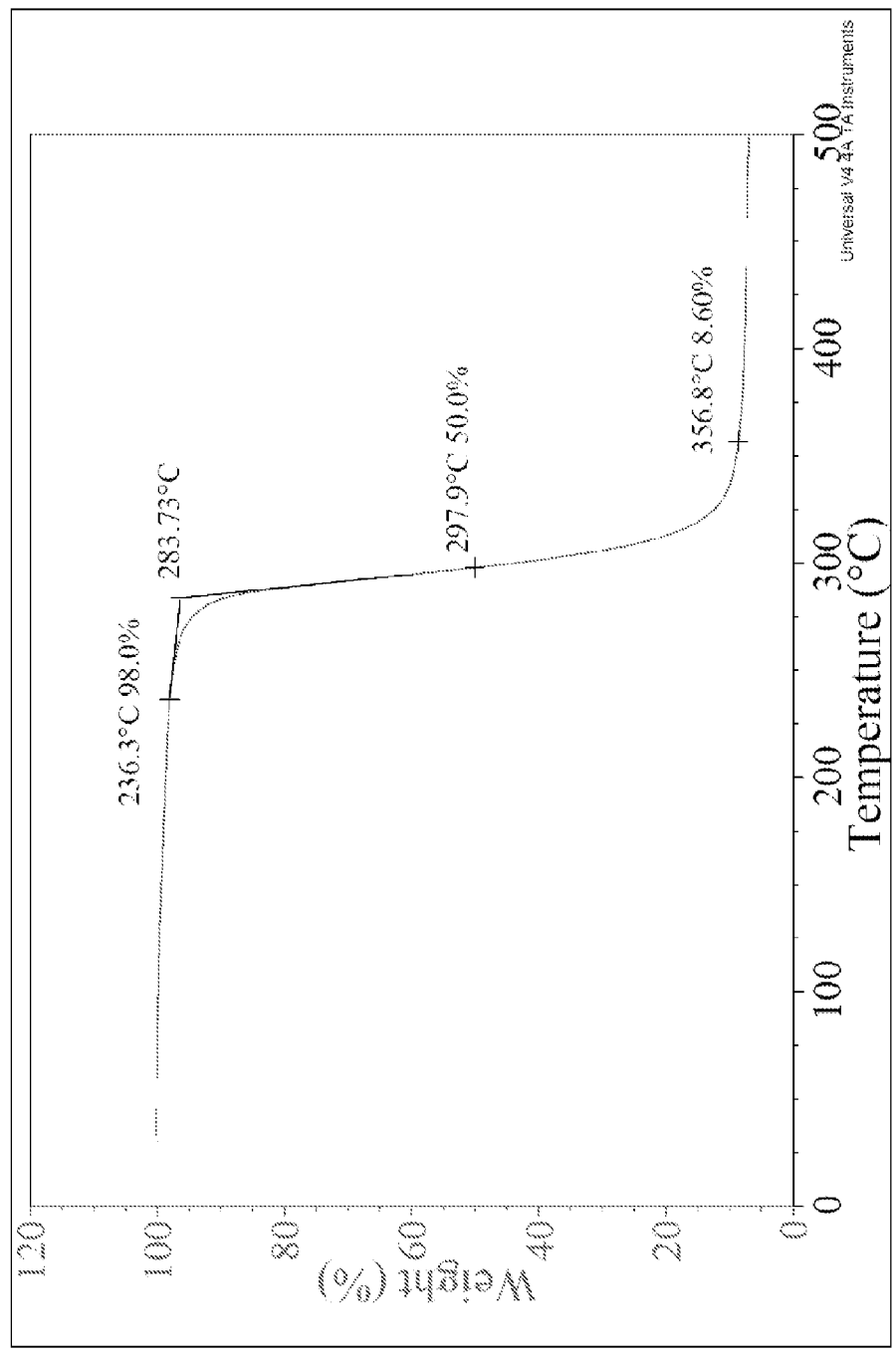
FIG. 18 is a TGA plot for the product of Example 4.
Figure 19:
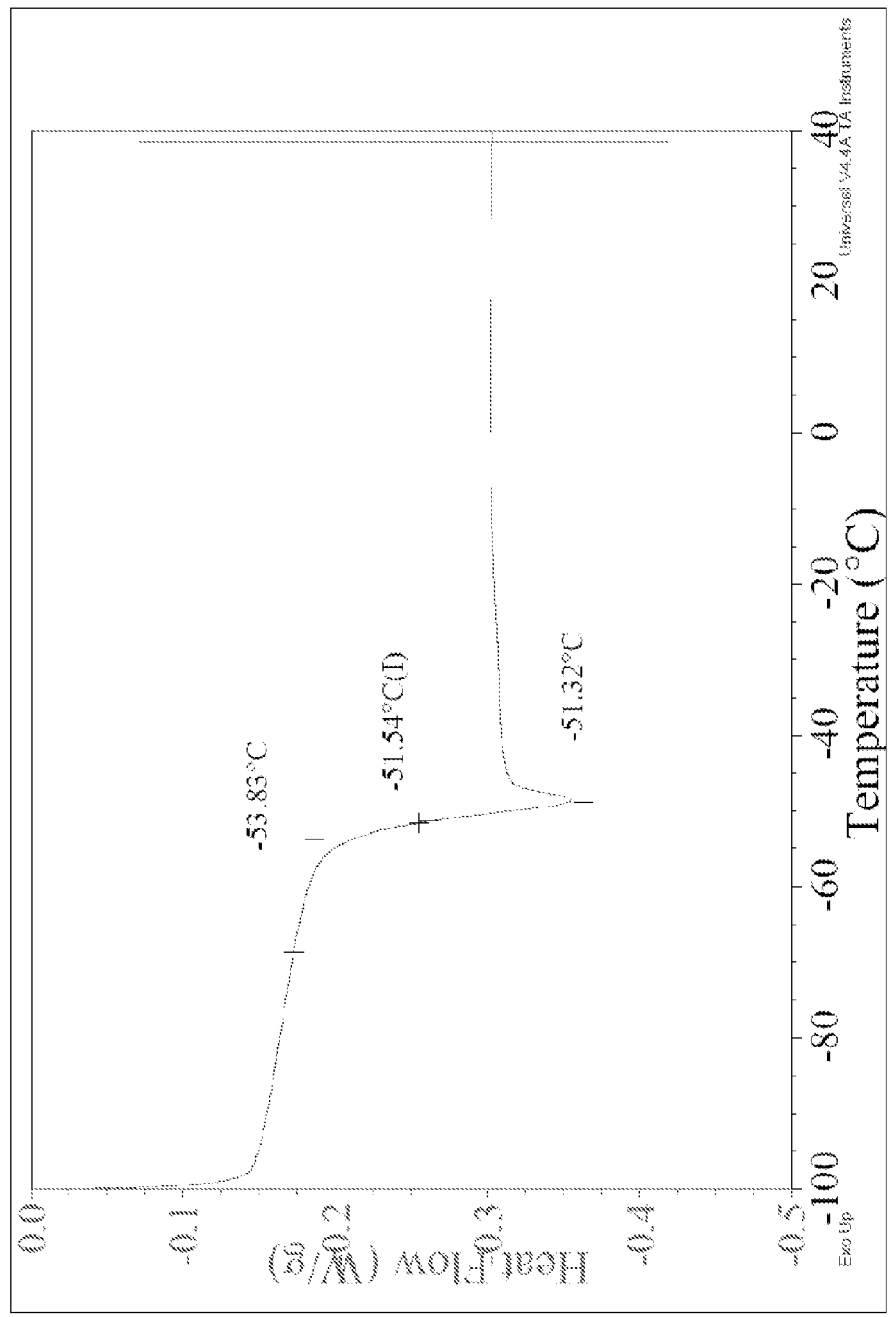
FIG. 19 is a DSC plot of the product of Example 4.

The NMR spectra of the polymer (not shown) were very similar to that shown in Example 3. This sample also showed one low temperature glass transition between −53.83° C. and −51.32° C., with no crystalline melting point (FIG. 19). The TGA decomposition trace (FIG. 18) shows 2% mass loss at 236.3° C., 50% mass loss at 297.9° C. and the decomposition plateau at 356.8° C. The thermal degradation temperature as calculated by the Universal Analysis software was 283.7° C.

Example 5

Figure 20:
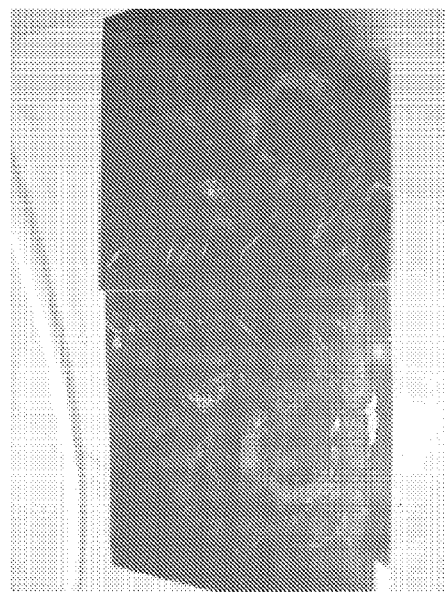
FIG. 20 is a pair of photographs showing the poly(ethanedisulfide) of Example 5 before (left) and after (right) compression molding.
Figure 20:
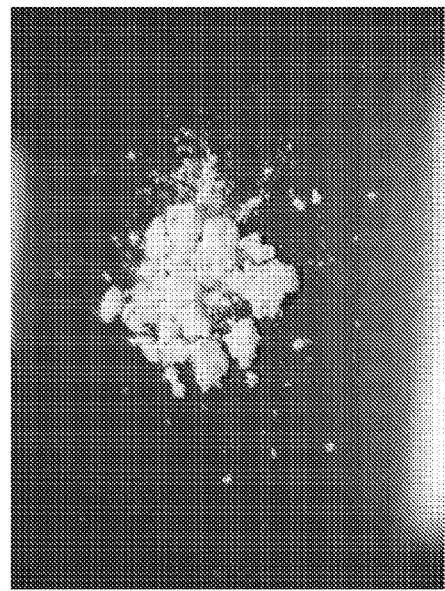
Figure 21A:
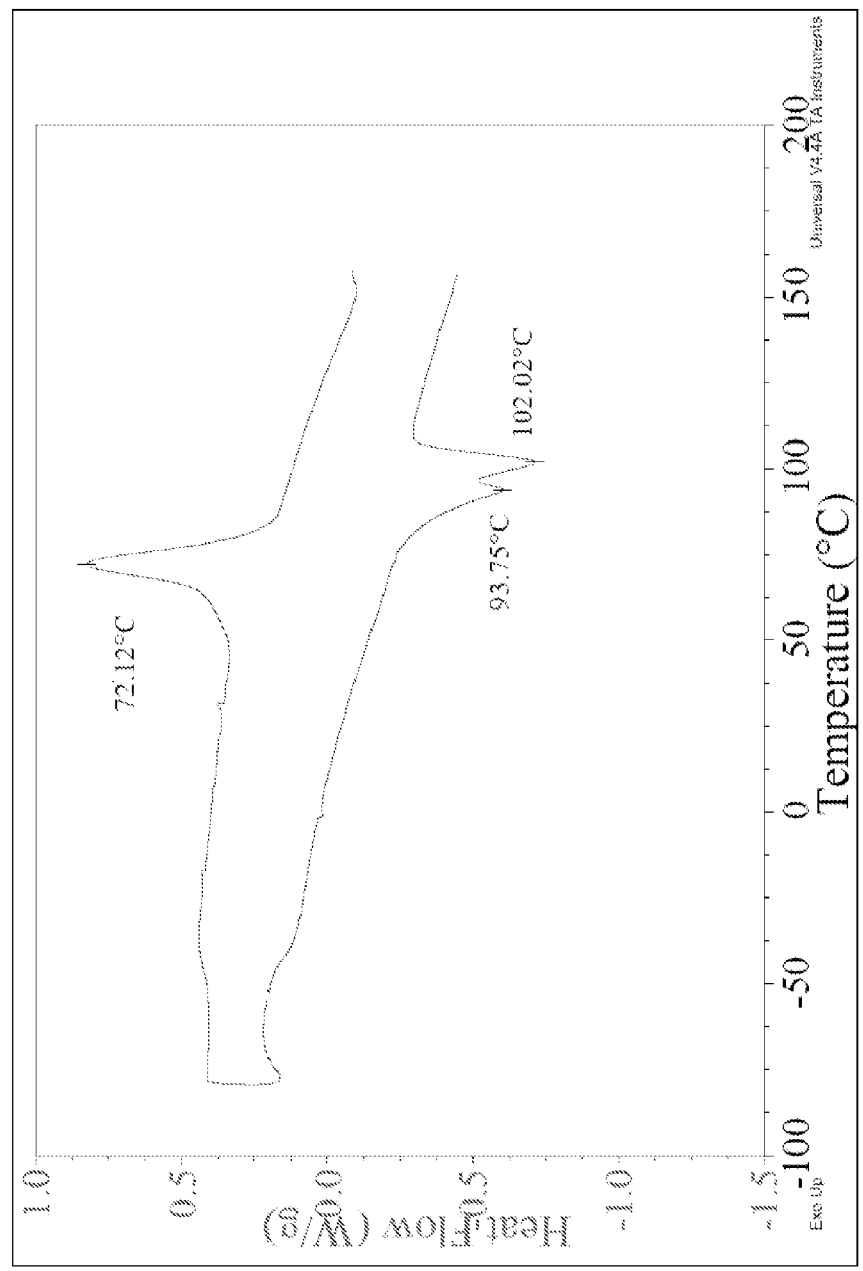
FIG. 21A is a full DSC plot of the product of Example 5.
Figure 21B:
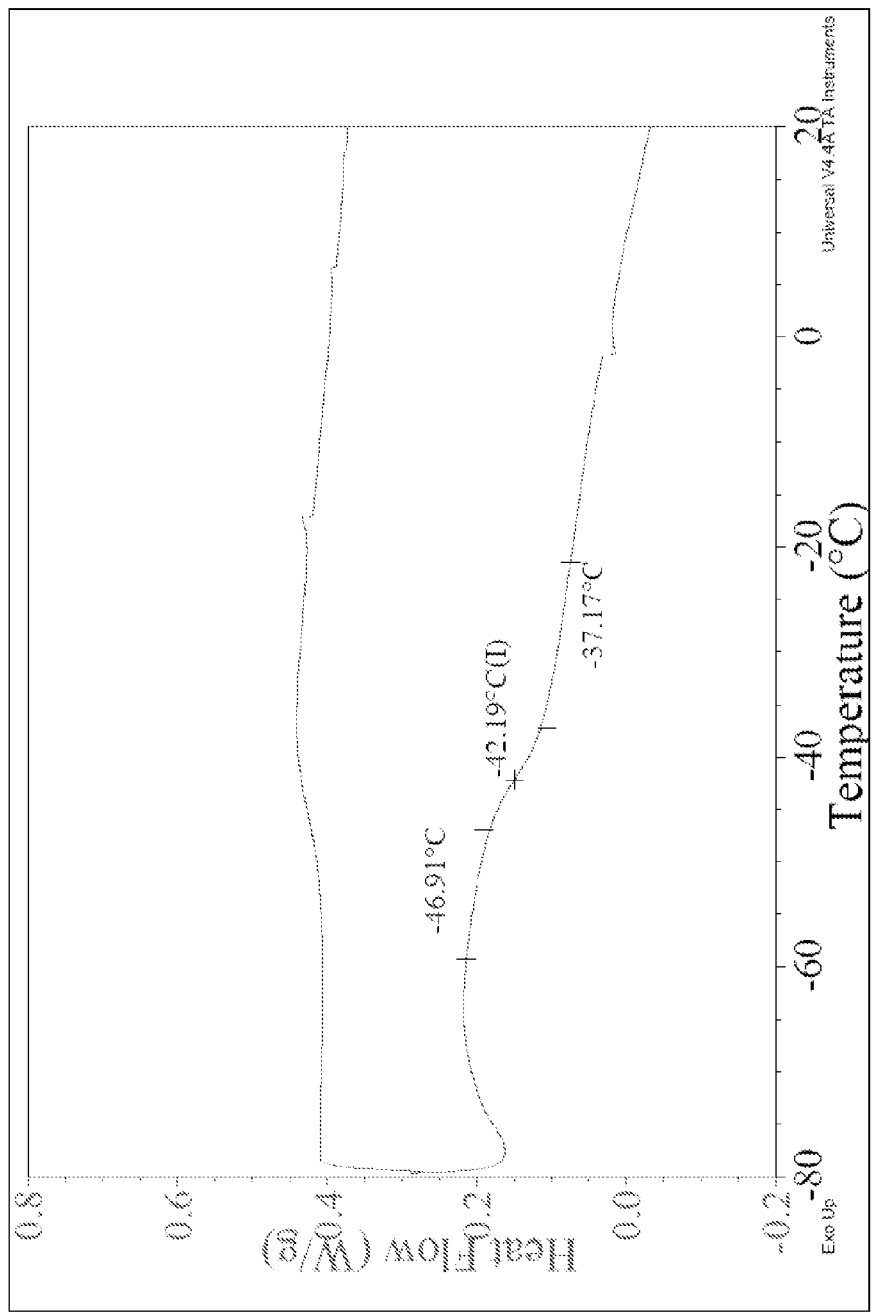
FIG. 21B is an enlarged detail of the glass transition region of the DSC plot of FIG. 21A.

Ethanedithiol (0.50 mL; 5.96 mmol; 0.17M) and 2,2'-[ethane-1,2diylbis(oxy)]diethanethiol (0.5 mL; 3.06 mmol; 0.09M) were reacted with triethylamine (2.94 mL; 21.1 mmol; 0.59M) and dilute aqueous hydrogen peroxide (2.0 mL of 3% aqueous solution; 1.8 mmol; 0.05M). After one hour, excess hydrogen peroxide was added (approx. 16 mL of 3% aqueous solution; 14.1 mmol, 0.39M). Air incorporation was achieved by agitation of the reaction flask. A polymer in the form of a coarse white powder was formed. The polymer was not soluble in organic solvents and was compression molded into a film (FIG. 20). The DSC analysis (FIG. 21A) of the polymeric product shows a weak low temperature glass transition, and strong melting/crystallization peaks, indicating that either a mixture of homopolymers, mostly poly (ethane disulphide), or a copolymer with ethanedithiol-rich blocks formed. FIG. 21A shows the full DSC trace. FIG. 21B shows the glass transition region of FIG. 21A in detail. The low temperature glass transition of the copolymer was about 10° C. higher than the glass transition temperature of the 2,2'-[ethane-1,2diylbis(oxy)]diethanethiol homopolymer. While again not wishing to condition patentability on any particular theory, this supports the idea of copolymer formation. The melting/crystallization peaks appear at a lower temperature than the melting/crystallization peaks of the ethanedithiol homopolymer in Examples 1 and 2. TGA of the polymer product (not shown) indicated that it started to degrade at 200° C., and had reached full decomposition by 300° C.

Example 6

The method of oxidation may also be used to create polymer networks linked by disulfide bonds. In this example, 2,2'-[ethane-1,2diylbis(oxy)]diethanethiol (2.05 mL; 12.54 mmol, 0.34M) was mixed with trimethylolpropane tris(3-mercaptopropionate) ($HSCH_2CH_2CO_2CH_2)_3CC_2H_5$; 0.03 mL; 0.08 mmol; 0.002M) and triethylamine (1.71 mL; 12.35 mmol; 0.34M). To the mixture, 3.0 mL tetrahydrofuran and 5.0 mL ethyl acetate were added. Tetrahydrofuran is a solvent for all reagents used in the reaction, while ethyl acetate is immiscible with the aqueous hydrogen peroxide solution. While once again not wishing to rely on any particular theory for patentability, it is believed that the mix of solvents may allow for slower oxidation, leading to gels with a more uniform texture. Hydrogen peroxide was then added (about 25 mL of 3% aqueous solution; 22.0 mmol; 0.60M), and air was bubbled into the reaction flask for 5 minutes. After the bubbling, the reagents were allowed to react undisturbed for 16 hours. The rubbery gel disk that formed was soaked in acetone for 6 hours and then dried in a vacuum oven for 24 hours. The mass of the dry gel was 1.3550 g indicating a conversion of 59.3%.

Figure 22:
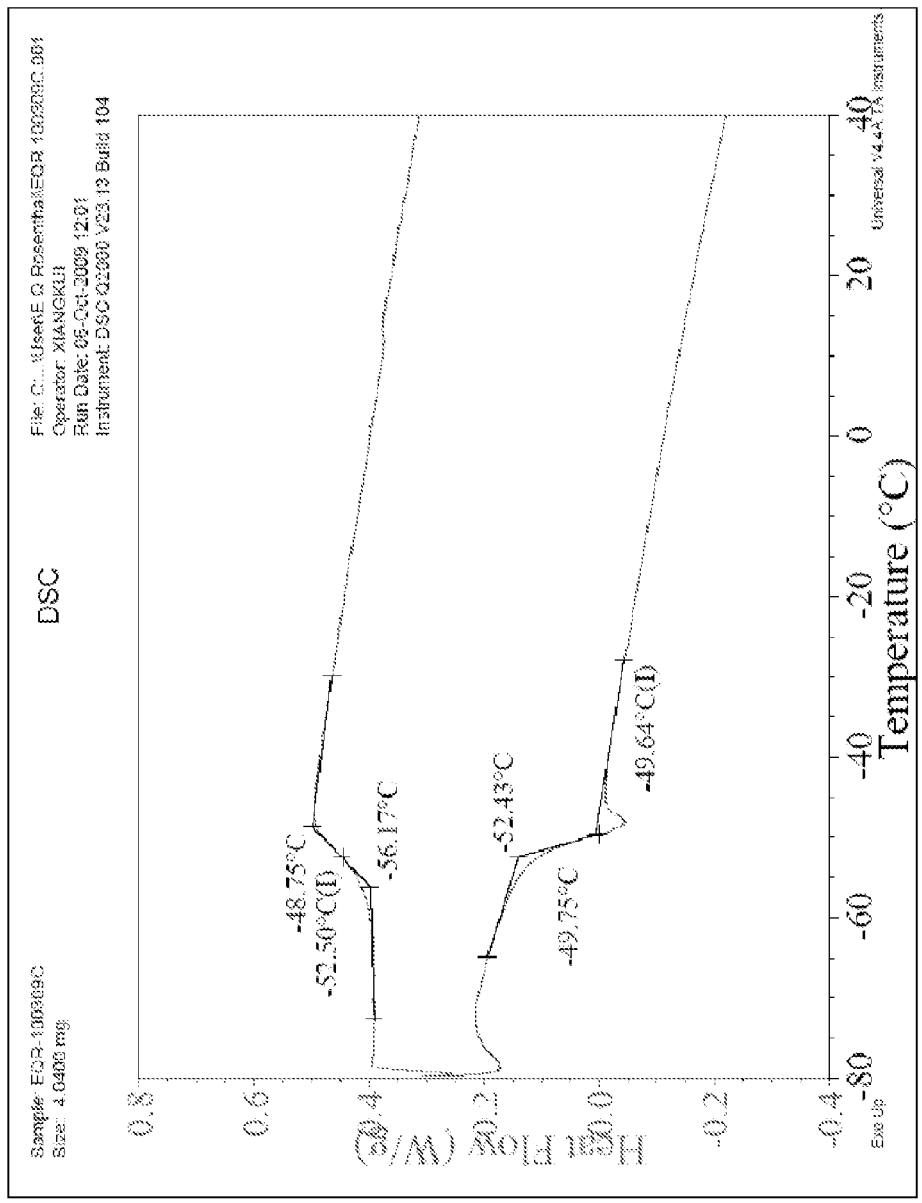
FIG. 22 is a DSC plot of the product of Example 6.

DSC analysis (FIG. 22) showed that the gel behaved similarly to the linear homopolymer upon heating. It did not show a crystallization peak and displayed a glass transition temperature range between −52.43° C. and −49.64° C. Preliminary solvent-swelling experiments showed that the gel swell strongly in tetrahydrofuran (327% mass increase), but did not swell in hexanes. In hexanes the mass was reduced in each sample by an average of 4.3% after swelling (Table 3), indicating very effective crosslinking. The gel described does not swell in water. Water absorbent hydrogels can be made by the same method using thiol functionalized poly(ethyleneglycol) as described more fully below. It is envisioned that the water swelling behavior can be controlled by the level of this latter in the monomer mixture.

TABLE 3

| Sample | Swelling Solvent | Mass (g) Dry Gel | Mass (g) Swollen Gel | % Change | Average % Change |
|---|---|---|---|---|---|
| 1 | THF | 0.0110 | 0.0429 | 290.0 | |
| 2 | THF | 0.0070 | 0.0316 | 351.4 | 327.08 |
| 3 | THF | 0.0113 | 0.0497 | 339.8 | |
| 4 | Hexanes | 0.0110 | 0.0105 | −4.5 | |
| 5 | Hexanes | 0.0086 | 0.0082 | −4.7 | −4.29 |
| 6 | Hexanes | 0.0109 | 0.0105 | −3.7 | |

In a variation of Example 6, carbon black was easily and uniformly incorporated in situ during the oxidation reaction reaction. The carbon black (Cabot, Black Pearls® 4350, specified for biomaterials) filled gel has a unique porous texture and increased strength. The easy incorporation of carbon black into the gel is promising because it indicates the breadth of possible materials that may be made by this new method. We found that carbon black improved the biocompatibility of hydrocarbon polymers. In addition, hydrogen peroxide may be used for sterilization, so the gels and polymers can be made under sterile conditions.

Polymers and gels made by this method have further utility as biomaterials because they contain disulfide bonds. Disulfide bonds are an ubiquitous motif in biological systems, and the thiol-disulfide interchange is a constant biological reaction. Sulfur-sulfur bonds can be efficiently degraded by enzymes and by reducing environments, including those found in biological systems. Previous work in disulfide biomaterials suggests that materials made in this invention will biodegrade.

Example 7

The dithiol monomer 2,2'-[ethane-1,2diylbis(oxy)]diethanethiol (DODT), and triethylamine (1:1.25 equivalent ratio) were mixed and reacted for 10 minutes. To the monomer mixture, 2.0 equivalents of hydrogen peroxide (3% aqueous solution by weight) were added in 10-15 aliquots of equal volume during a time period of 15-20 minutes to keep the reaction temperature below 55° C. The final concentrations for DODT, triethylamine and hydrogen peroxide were 0.36M, 0.69M and 0.90M respectively. It should be noted, however, that polymer started to precipitate after the addition of about one equivalent of hydrogen peroxide. Air was then bubbled into the reaction flask while maintaining vigorous stirring using a magnetic stir bar in an open environment for 2 hours. The precipitated polymer was then removed from the reaction flask, rinsed with water and extracted with acetone for 72 hours (refreshed every 24 hours) to remove residual triethylamine and monomer. The excess acetone was decanted and the polymer was dried in a vacuum oven until constant weight was achieved. The conversion of the polymer was 90%. The polymer was then analyzed by NMR, FTIR, and MALDI-ToF providing data consistent with the previously described DODT polymers. The molecular weight data from the SEC for three samples is given in Table 4.

TABLE 4

| Sample | Molecular Weight $M_n$ (g/mol) | Molecular Weight $M_w$ (g/mol) | PDI ($M_w/M_n$) |
|---|---|---|---|
| 7A | 14000 | 19000 | 1.35 |
| 7B | 47000 | 84000 | 1.79 |
| 7C | 230000 | 345000 | 1.50 |

Figure 23:
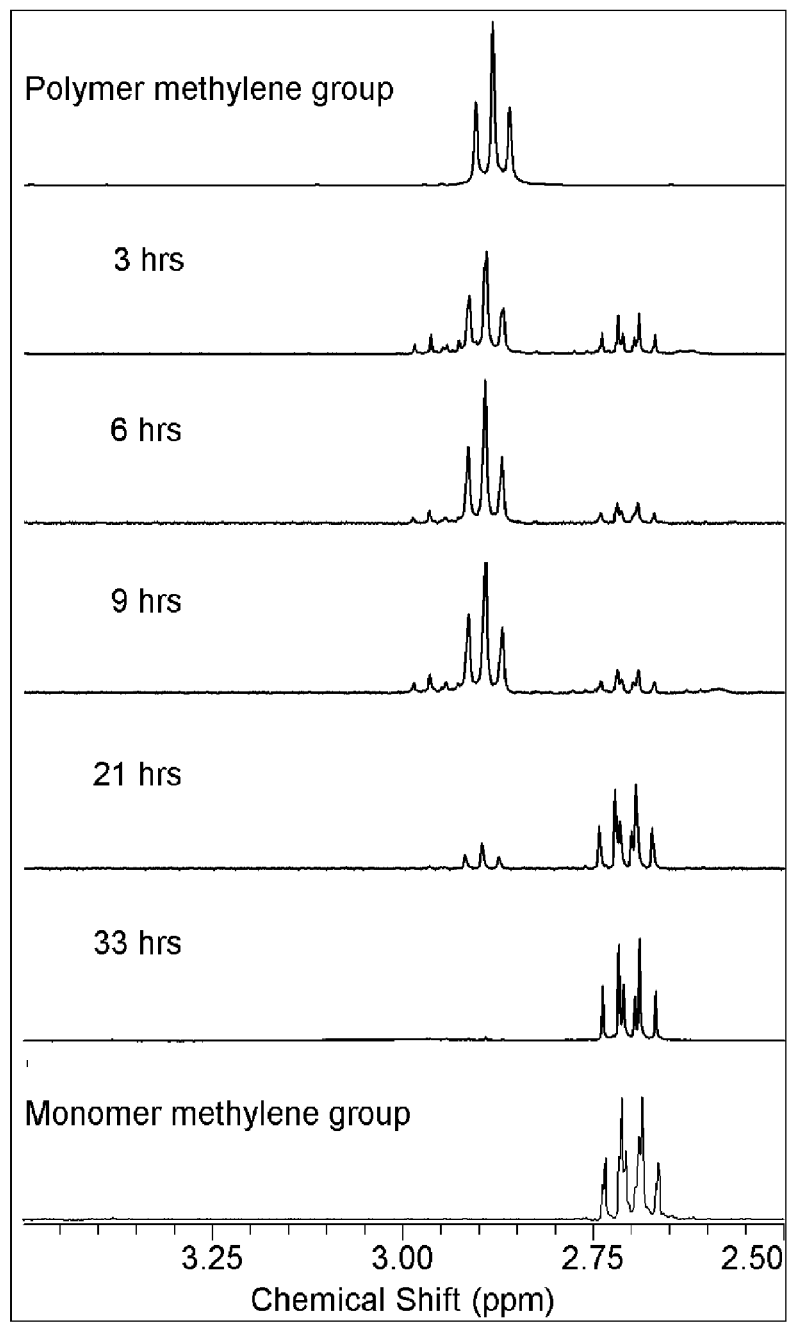
FIG. 23 is a time course of $^1$H NMR spectra showing degradation of the product of Example 7 by dithiothreitol (DTT).

To determine biodegradability, the polymer of Example 7C was degraded using dithiothreitol (DTT), a disulfide-specific reducing agent, as follows. In a 500 mL round-bottomed flask, 0.3123 g of polymer was dissolved in 100 mL of THF and 40 mL of a 50.05 mM aqueous DTT solution was added to the flask. The mixture was stirred vigorously with a magnetic stir bar. Aliquots (10 mL) were taken at timed intervals for NMR analysis. The reduction reaction was stopped by adding 5 mL of chloroform and 5 mL of saturated NaCl solution to the aliquot which separated the polymer and monomer from the DTT. The organic phase was then dried and analyzed by NMR. FIG. 23 provides a time course of proton NMR spectra showing the essentially complete degradation of the polymer by DTT. This indicates that the polymer consists essentially of disulfide bonds between units of the polymer. Because disulfide bonds are degraded to thiols in biological systems, this indicates that the claimed invention provides polymers that are biodegradable.

Example 8

Tetraethyleneglycol diacrylate (TEG-DA) may be functionalized with trimethylolpropane tris(3-mercaptopropionate) via thiol-ene click chemistry to create a tetrathiol fuctionalized molecule according to the scheme:

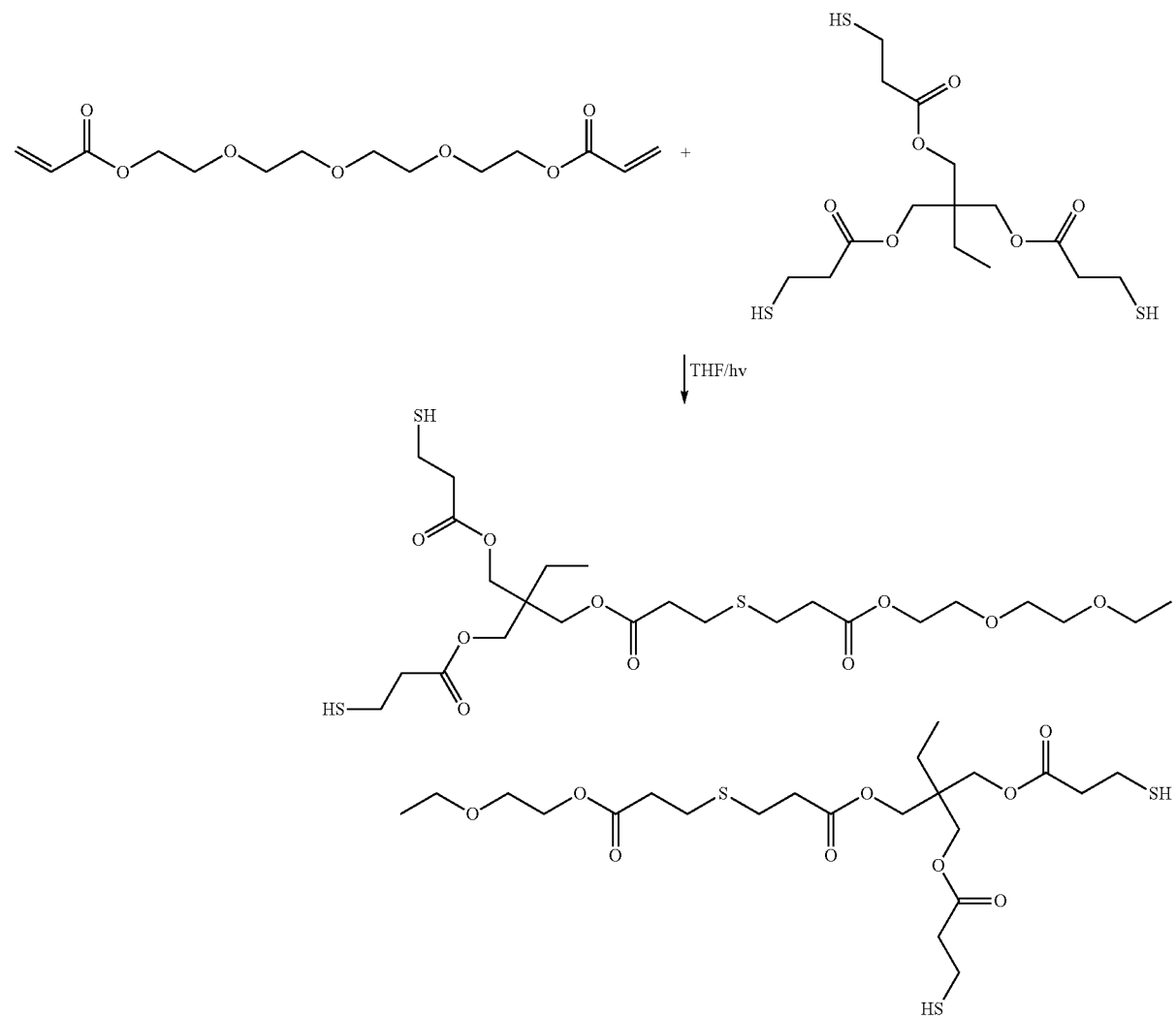

Figure 24:
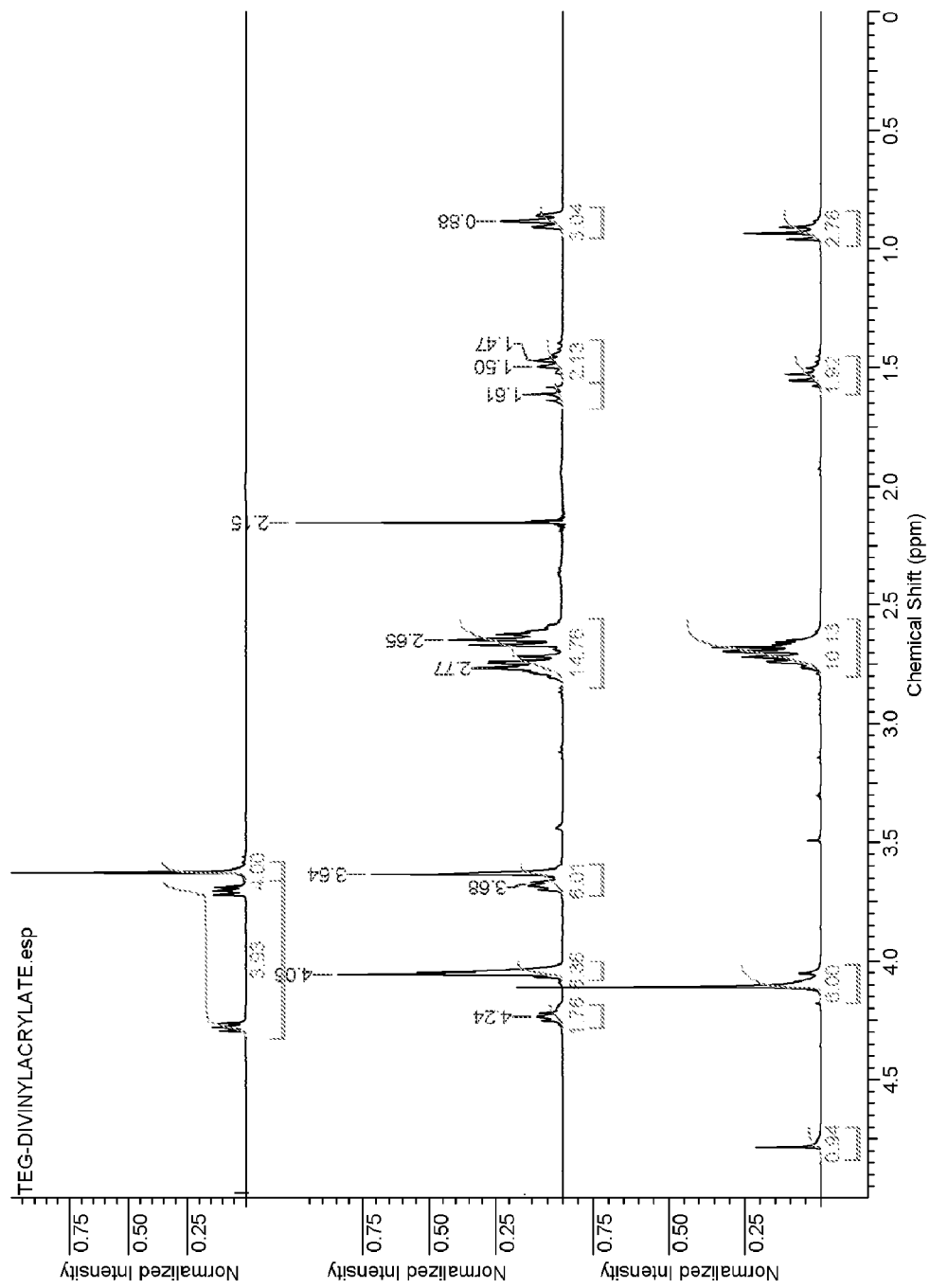
FIG. 24 is the NMR spectra for the starting materials (top and bottom) and the product (center) of Example 8.

To a 50 mL flask equipped with a stirbar, 7 mL of THF, 2 mL of TEG-DA and 5 mL of trimethylopropane tri(3-mercapto propionate) were added and stirred. A UV lamp was set up next to the stirring flask and aluminum foil was used to encase both flask and lamp. The sample was subjected to UV exposure for one hour. The flask was placed on the rotavap to remove THF. The product was filtered and analyzed by NMR, shown in FIG. 24. The starting materials are shown on top (TEG-DA) and at the bottom (trimethylolpropane tris(3-mercaptopropionate)) with the product in the middle of FIG. 24.

Example 9

A biodegradable and chemically crosslinked polymer network may be prepared using the product of Example 8. To a 4 mL vial, 0.31 mL of product from Example 8 was added with 1 mL triethylamine ($Et_3N$). The two liquids were not miscible, so THF was added (1 mL) to dissolve the reagents. Next, 2 mL of $H_2O_2$ (3% wt. Aq.) was added and the vial was shaken to mix ingredients. The contents of the vial almost instantly formed a white, waxy substance which was removed from the vial and filtered and rinsed with deionized H$_2$O. Before drying, the solids weighed 1.0221 g. After drying they weighed 0.2111 g. These masses are more important to give an idea of swelling rather than yield. The dry gel is both rubbery and crumbly at the same time. A piece was chosen for swelling in water. The dry mass was 0.0238 g, the swollen mass at equilibrium was 0.0376 g, which gives a mass gain of 0.0138 g or 58.0%.

Example 10

Poly(isobutylene) (PIB, chemical formula (C$_4$H$_8$)$_n$) is a well-established biocompatible polymer with a low glass transition temperature. PIB chains with thiol functionalization at the α- and ω-positions may be linked together via disulfide bonds created using the newly developed oxidizing system. Dithiol PIB may be dissolved in THF and triethylamine added to the polymer solution in a 2.25:1 molar ratio with PIB. Hydrogen peroxide (aqueous 3% by weight) may be added to the solution in a 2:1 molar ration with dithiol PIB while bubbling in air and stirring vigorously for two hours. THF may be added as needed to prevent polymer precipitation. The polymer may be purified by dissolving it in THF and precipitating it into a cold methanol/acetone mixture. The resulting polymer is expected to be a high molecular weight PIB-disulfide, containing blocks of poly(isobutlylene) connected by disulfide bonds. The average number of disulfide bonds in each chain is expected to be about 3.

Example 11

Liquid (PIB) (low molecular weight chains, approx. 500-10,000 g/mol) with thiol functionalization at the α- and ω-positions may be linked together via disulfide bonds using the newly developed oxidizing system. PIB may be reacted with triethylamine in bulk in a 2.25:1 molar ratio with dithiol-PIB. Hydrogen peroxide may be added to the solution while bubbling in air and stirring vigorously in a 2:1 ratio with dithiol PIB. PIB-disulfide precipitates from the solution. The polymer may be purified by dissolving it in THF and precipitating it into a cold methanol/acetone mixture. The resulting polymer is expected to be a high molecular weight PIB-disulfide, containing blocks of poly(isobutlylene) connected by disulfide bonds. The average number of disulfide bonds in each chain is expected to be 8.

Example 12

The α,ω-thiol functionalized poly(isobutylene) chains from Example 10 or other dithiol functionalized PIB chains like those in Example 11 may also be used to create a network using the method established in Example 6. Dithiol functionalized PIB may be dissolved in THF and reacted with triethylamine in a 2.25:1 molar ration of amine to PIB. Ethyl acetate can be added in a 5:3 volume ratio with THF, as described in Example 6. To the mixture, hydrogen peroxide may be added in a 2:1 ratio with the PIB.

Example 13

Poly(ethylene glycol) (PEG, chemical formula, HOCH$_2$CH$_2$(OCH$_2$CH$_2$)$_n$OH) is a highly versatile, water soluble polymer that has been used in the biomedical field for decades. PEG chains with thiol functionalization at the α- and ω-positions may be linked together via disulfide bonds created using the newly developed oxidizing system. Dithiol PEG may be dissolved in deionized water and stirred for two hours to ensure dissolution. Triethylamine may be added to the polymer solution in a 2.25:1 molar ratio with dithiol PEG. Hydrogen peroxide (aqueous 3% by weight) can be added to the solution in a 2:1 molar ratio with dithiol PEG while bubbling in air and stirring vigorously for two hours, for example. The polymer may be purified by precipitation into cold ethanol. The resulting polymer is expected to be a high molecular weight PEG-disulfide, containing blocks of poly(ethylene glycol) connected by disulfide bonds. The average number of disulfide bonds per chain is expected to be 4.

Example 14

Tetraethylene glycol, or TEG, is a liquid, short chain analog of poly(ethylene glycol) containing 4 repeating ethylene glycol units (chemical formula, HOCH$_2$CH$_2$(OCH$_2$CH$_2$)$_n$OH where n=3). TEG chains with thiol functionalization at the α- and ω-positions may be linked together via disulfide bonds created using the newly developed oxidizing system. Dithiol TEG may be dissolved in a 25:75 mix of deionized water and tetrahydrofuran. Triethylamine can be added to the reaction solution in a 2.25:1 molar ratio with TEG. Hydrogen peroxide (aqueous 3% by weight) may be added to the solution in a 2:1 molar ratio with dithiol TEG while bubbling in air and stirring vigorously for two hours. The reaction flask may be then subjected to rotary evaporation to concentrate the reaction solution. The concentrated solution can then be purified by precipitation into cold ethanol. The resulting product is predicted to be a rubbery polymer with a similar appearance to the DODT polymer described previously (Example 3).

Example 15

It is anticipated that the length of TEG-disulfide polymer chains may be regulated by the addition of the biological monothiol cysteine (an essential amino acid). TEG chains with thiol functionalization at the α- and ω-positions may be linked together via disulfide bonds created using the oxidizing system of the claimed invention. Dithiol TEG can be stirred in a 90:10 mix of deionized water and tetrahydrofuran until dissolved. Triethylamine may be added to the reaction solution in a 2.25:1 molar ratio with dithiol TEG. An aqueous solution (0.08M for example) of the cysteine hydrochloride monohydrate with at pH of between 6.5 and 7.0 can then be added. Hydrogen peroxide (aqueous 3% by weight) may be added to the solution in a 2:1 molar ratio with dithiol TEG while bubbling in air and stirring vigorously for two hours. The reaction flask can then be subjected to rotary evaporation to concentrate the reaction solution. The concentrated solution was then purified by precipitation into cold ethanol. Elman's reagent may be used to determine the number of disulfide bonds formed. By comparing the total mass and molecular weight of the starting material and product, the average number of disulfide bonds per chain may be determined and is expected to be 30±7.

Based upon the foregoing disclosure, it should be evident that the claimed invention is highly effective in providing an alternate method of synthesis of organic poly(disulfide) polymers that avoids dangerous or toxic oxidation methods by oxidation using the oxidizing capabilities of hydrogen peroxide and oxygen with a heavy metal-free catalyst. The invention is also effective in providing a method of synthesis of organic poly(disulfide) polymers that has the ability to polymerize a variety of dithiol monomers to high molecular weights. The claimed method may also be applied to the polymerization of α,ω-dithiol prepolymers and oligomers. Additionally, it is an effective method for the formation of

What we claim is:

1. A method for the synthesis of poly(disulfide) polymers, the method comprising:
   providing a dithiol composition, and
   subjecting the dithiol composition to an oxidizing environment in the presence of a tertiary amine catalyst in an aqueous solution to provide a polydisulfide polymer.

2. The method of claim 1, wherein the dithiol composition comprises at least one dithiol compound selected from the group consisting of aliphatic dithiols and alkoxy dithiols.

3. The method of claim 2, wherein the dithiol composition is a $C_2$-$C_{15}$ compound.

4. The method of claim 2, wherein the dithiol composition is selected from the group consisting of ethanedithiol, 2,2'[ethane-1,2diylbis(oxy)]diethanethiol, α,ω-thiol functionalized tetraethylene glycol, α,ω-thiol functionalized poly(isobutylene), α,ω-thiol fuctionalized poly(ethylene glycol) and combinations thereof.

5. The method of claim 4, wherein the dithiol composition comprises ethanedithiol, 2,2'-[ethane-1,2diylbis(oxy)]diethanethiol, or a combination thereof.

6. The method of claim 4, wherein the oxidizing environment is provided by the presence of hydrogen peroxide and atmospheric oxygen.

7. The method of claim 6, wherein the step of subjecting the dithiol composition to an oxidizing environment takes place in the additional presence of a solvent in which the hydrogen peroxide is immiscible, wherein the solvent in which the hydrogen peroxide is immiscible is ethyl acetate.

8. The method of claim 1, wherein the step of subjecting the dithiol composition to an oxidizing environment additionally takes place in the additional presence of a trithiol compound and results in a crosslinked poly(disulfide) polymer network.

9. The method of claim 8, wherein the trithiol compound is trimethylolpropane tris(3-mercaptopropionate).

10. The method of claim 1, wherein the step of subjecting the dithiol composition to an oxidizing environment additionally takes place in the presence of a monothiol compound.

11. The method of claim 10, wherein the monothiol compound is cysteine.

12. The method of claim 1, wherein the step of subjecting the dithiol composition to an oxidizing environment additionally takes place in the presence of a filler which becomes incorporated into the poly(disulfide) polymer.

13. The method of claim 12, wherein the filler is carbon black.

14. The method of claim 2, wherein the aliphatic dithiol is a $C_2$-$C_{15}$ compound.

15. The method of claim 2, wherein the alkoxy dithiol is a $C_2$-$C_{15}$ compound.

16. The method of claim 1, wherein the polydisulfide polymer has a weight average molecular weight of greater than about 100,000 g/mol and a polydispersity index of about 2 or less.

17. The method of claim 1, wherein said step of subjecting the dithiol composition to an oxidizing environment in the presence of tertiary amine catalyst in an aqueous solution to provide a polydisulfide polymer occurs in less than 2 hours.

18. The method of claim 1, wherein the tertiary amine catalyst is triethylamine.

* * * * *